US009945837B2

(12) United States Patent
Dupoteau et al.

(10) Patent No.: US 9,945,837 B2
(45) Date of Patent: *Apr. 17, 2018

(54) SINGLE-USE HANDHELD DIAGNOSTIC TEST DEVICE, AND AN ASSOCIATED SYSTEM AND METHOD FOR TESTING BIOLOGICAL AND ENVIRONMENTAL TEST SAMPLES

(71) Applicant: FIO CORPORATION, Toronto (CA)

(72) Inventors: Francois Dupoteau, Toronto (CA); Shlomit Dekel, Toronto (CA)

(73) Assignee: FIO CORPORATION, Toronto (CA)

( * ) Notice: Subject to any disclaimer, the term of this patent is extended or adjusted under 35 U.S.C. 154(b) by 35 days.

This patent is subject to a terminal disclaimer.

(21) Appl. No.: 15/258,423

(22) Filed: Sep. 7, 2016

(65) Prior Publication Data
US 2016/0377593 A1    Dec. 29, 2016

Related U.S. Application Data

(63) Continuation of application No. 13/061,284, filed as application No. PCT/CA2009/001206 on Aug. 31, 2009, now Pat. No. 9,459,200.
(Continued)

(51) Int. Cl.
*G01N 37/00*    (2006.01)
*G01N 33/487*    (2006.01)
(Continued)

(52) U.S. Cl.
CPC ..... *G01N 33/48792* (2013.01); *A61B 5/0077* (2013.01); *A61B 5/1171* (2016.02);
(Continued)

(58) Field of Classification Search
None
See application file for complete search history.

(56) References Cited

U.S. PATENT DOCUMENTS

| 5,244,630 A | 9/1993 | Khalil et al. |
| 5,662,824 A | 9/1997 | Sang et al. |

(Continued)

FOREIGN PATENT DOCUMENTS

| CA | 2021587 | 8/1992 |
| CA | 2061574 | 4/2003 |

(Continued)

OTHER PUBLICATIONS

Gupta, P. et al. Efficient fingerprint-based user authentication for embedded systems, 2005, DAC 2005, Jun. 13-17, 2005, Anaheim, California, USA, pp. 244-247.
(Continued)

*Primary Examiner* — Xiaoyun R Xu
(74) *Attorney, Agent, or Firm* — SmithAmundsen LLC; Jennifer Lacroix

(57) ABSTRACT

In a single-use handheld diagnostic test device and an associated system and method, a biological and/or environmental test sample is received and reacted with reagents. The test device tests a single sample and includes a sensor to detect test data. The test device mates with, and transmits the test data to, an electronic device. A processor of the electronic device applies algorithms to the test data to generate highly sensitive and accurate quantitative test results. A presentation element of the electronic device presents the test results to a user. The test device is adapted for disposal, or for sterilization and re-use, after the electronic device receives the test data. The electronic device may be, for example, a mobile communications device, a personal digital assistant, a laptop computer, a navigation device, a digital audio player, a camera, or a gaming device.

30 Claims, 9 Drawing Sheets

Related U.S. Application Data

(60) Provisional application No. 61/144,283, filed on Jan. 13, 2009, provisional application No. 61/093,036, filed on Aug. 29, 2008.

(51) Int. Cl.
*A61B 5/1172* (2016.01)
*G01N 21/77* (2006.01)
*G06F 19/00* (2018.01)
*G01N 21/17* (2006.01)
*A61B 5/1171* (2016.01)
*A61B 5/00* (2006.01)

(52) U.S. Cl.
CPC .......... *A61B 5/1172* (2013.01); *A61B 5/1176* (2013.01); *G01N 21/17* (2013.01); *G01N 21/77* (2013.01); *G06F 19/3406* (2013.01); *Y10T 436/12* (2015.01)

(56) References Cited

U.S. PATENT DOCUMENTS

| | | |
|---|---|---|
| 5,714,390 A | 2/1998 | Hallowitz et al. |
| 5,786,219 A | 7/1998 | Zhang et al. |
| 5,817,458 A | 10/1998 | King et al. |
| 5,837,442 A | 11/1998 | Tsang |
| 6,011,252 A | 1/2000 | Jensen |
| 6,022,500 A | 2/2000 | John et al. |
| 6,066,243 A | 5/2000 | Anderson et al. |
| 6,100,541 A | 8/2000 | Nagle et al. |
| 6,103,379 A | 8/2000 | Margel et al. |
| 6,114,038 A | 9/2000 | Castro et al. |
| 6,119,953 A | 9/2000 | Ganan-Calvo et al. |
| 6,172,193 B1 | 1/2001 | Primi et al. |
| 6,174,469 B1 | 1/2001 | Ganan-Calvo |
| 6,261,779 B1 | 6/2001 | Barbera-Guillem et al. |
| 6,274,323 B1 | 8/2001 | Bruchez et al. |
| 6,309,701 B1 | 10/2001 | Barbera-Guillem |
| 6,316,781 B1 | 11/2001 | Nagle et al. |
| 6,319,607 B1 | 11/2001 | Barbera-Guillem et al. |
| 6,333,110 B1 | 12/2001 | Barbera-Guillem |
| 6,340,588 B1 | 1/2002 | Nova et al. |
| 6,353,475 B1 | 3/2002 | Jensen et al. |
| 6,357,670 B2 | 3/2002 | Ganan-Calvo |
| 6,399,952 B1 | 6/2002 | Maher et al. |
| 6,409,900 B1 | 6/2002 | Parce et al. |
| 6,413,401 B1 | 7/2002 | Chow et al. |
| 6,430,512 B1 | 8/2002 | Gallagher |
| 6,468,808 B1 | 10/2002 | Nie et al. |
| 6,494,830 B1 | 12/2002 | Wessel |
| 6,498,353 B2 | 12/2002 | Nagle et al. |
| 6,504,607 B2 | 1/2003 | Jensen et al. |
| 6,506,609 B1 | 1/2003 | Wada et al. |
| 6,514,399 B1 | 2/2003 | Parce et al. |
| 6,524,793 B1 | 2/2003 | Chandler et al. |
| 6,528,165 B2 | 3/2003 | Chandler |
| 6,544,732 B1 | 4/2003 | Chee et al. |
| 6,548,171 B1 | 4/2003 | Barbera-Guillem et al. |
| 6,548,264 B1 | 4/2003 | Tan et al. |
| 6,554,202 B2 | 4/2003 | Ganan-Calvo |
| 6,576,155 B1 | 6/2003 | Barbera-Guillem |
| 6,592,821 B1 | 7/2003 | Wada et al. |
| 6,592,822 B1 | 7/2003 | Chandler |
| 6,630,307 B2 | 10/2003 | Bruchez et al. |
| 6,632,655 B1 | 10/2003 | Mehta et al. |
| 6,649,138 B2 | 11/2003 | Adams et al. |
| 6,673,662 B2 | 1/2004 | Singh |
| 6,680,211 B2 | 1/2004 | Barbera-Guillem et al. |
| 6,699,723 B1 | 3/2004 | Weiss et al. |
| 6,720,411 B2 | 4/2004 | Mirkin et al. |
| 6,734,420 B2 | 5/2004 | Empedodes et al. |
| 6,740,491 B2 | 5/2004 | Mirkin et al. |
| 6,752,966 B1 | 6/2004 | Chazan |
| 6,759,235 B2 | 7/2004 | Empedodes et al. |
| 6,767,706 B2 | 7/2004 | Quake et al. |
| 6,772,070 B2 | 8/2004 | Gilmanshin et al. |
| 6,773,812 B2 | 8/2004 | Chandler et al. |
| 6,778,724 B2 | 8/2004 | Wang et al. |
| 6,787,088 B2 | 11/2004 | Parce et al. |
| 6,835,326 B2 | 12/2004 | Barbera-Guillem |
| 6,872,249 B2 | 3/2005 | Peng et al. |
| 6,881,537 B1 | 4/2005 | Goudsmit et al. |
| 6,881,821 B2 | 4/2005 | Simmonds et al. |
| 6,890,764 B2 | 5/2005 | Chee et al. |
| 6,905,885 B2 | 6/2005 | Colsten et al. |
| 6,966,880 B2 | 11/2005 | Boecker et al. |
| 6,978,212 B1 | 12/2005 | Sunshine |
| 6,986,837 B2 | 1/2006 | Chow et al. |
| 7,037,729 B2 | 5/2006 | Nie et al. |
| 7,041,362 B2 | 5/2006 | Barbera-Guillem |
| 7,069,191 B1 | 6/2006 | Moore |
| 7,077,328 B2 | 7/2006 | Kirchnaswamy et al. |
| 7,079,241 B2 | 7/2006 | Empedodes et al. |
| 7,166,475 B2 | 1/2007 | Colyer et al. |
| 7,171,983 B2 | 2/2007 | Chien et al. |
| 7,192,785 B2 | 3/2007 | Nie et al. |
| 7,243,670 B2 | 7/2007 | Witt et al. |
| 7,252,928 B1 | 8/2007 | Hafeman et al. |
| 7,267,799 B1 | 9/2007 | Borich et al. |
| 2001/0027918 A1 | 10/2001 | Parce et al. |
| 2001/0028055 A1 | 10/2001 | Fafard et al. |
| 2001/0046602 A1 | 11/2001 | Chandler et al. |
| 2001/0055764 A1 | 12/2001 | Empedodes et al. |
| 2002/0009728 A1 | 1/2002 | Bittner et al. |
| 2002/0022273 A1 | 2/2002 | Empedodes et al. |
| 2002/0031783 A1 | 3/2002 | Empedodes et al. |
| 2002/0037499 A1 | 3/2002 | Quake et al. |
| 2002/0045045 A1 | 4/2002 | Adams et al. |
| 2002/0048425 A1 | 4/2002 | McBride et al. |
| 2002/0051971 A1 | 5/2002 | Stuelpnagel et al. |
| 2002/0059030 A1 | 5/2002 | Otworth et al. |
| 2002/0066401 A1 | 6/2002 | Peng et al. |
| 2002/0118355 A1 | 8/2002 | Worthington et al. |
| 2002/0144644 A1 | 10/2002 | Zehnder et al. |
| 2002/0164271 A1 | 11/2002 | Ho |
| 2002/0182609 A1 | 12/2002 | Arcot |
| 2003/0003441 A1 | 1/2003 | Colston et al. |
| 2003/0017264 A1 | 1/2003 | Treadway et al. |
| 2003/0026740 A1 | 2/2003 | Staats |
| 2003/0073086 A1 | 4/2003 | Guire et al. |
| 2003/0099940 A1 | 5/2003 | Empedodes et al. |
| 2003/0132538 A1 | 7/2003 | Chandler |
| 2003/0148544 A1 | 8/2003 | Lauks |
| 2003/0157327 A1 | 8/2003 | Barbera-Guillem et al. |
| 2003/0148530 A1 | 9/2003 | Drucker et al. |
| 2003/0165951 A1 | 9/2003 | Bruchez, Jr. et al. |
| 2003/0170613 A1 | 9/2003 | Straus et al. |
| 2003/0172043 A1 | 9/2003 | Guyon et al. |
| 2003/0175773 A1 | 9/2003 | Chee et al. |
| 2003/0176183 A1 | 9/2003 | Drucker et al. |
| 2003/0177038 A1 | 9/2003 | Rao |
| 2003/0177941 A1 | 9/2003 | Barbera-Guillem |
| 2003/0190628 A1 | 10/2003 | Nakao et al. |
| 2003/0194350 A1 | 10/2003 | Stamatelos et al. |
| 2004/0009341 A1 | 1/2004 | Naasani |
| 2004/0067485 A1 | 4/2004 | Mayes et al. |
| 2004/0072428 A1 | 4/2004 | Sato et al. |
| 2004/0096363 A1 | 5/2004 | Porter |
| 2004/0101621 A1 | 5/2004 | Adams et al. |
| 2004/0106218 A1 | 6/2004 | Wang et al. |
| 2004/0118684 A1 | 6/2004 | Wainright et al. |
| 2004/0147031 A1 | 7/2004 | Nakao |
| 2004/0176704 A1 | 9/2004 | Stevens et al. |
| 2004/0203170 A1 | 10/2004 | Barbera-Guillem |
| 2004/0204633 A1 | 10/2004 | Rentea et al. |
| 2004/0229261 A1 | 11/2004 | Young |
| 2004/0241424 A1 | 12/2004 | Barbera-Guillem |
| 2004/0241752 A1 | 12/2004 | Anderson et al. |
| 2004/0247861 A1 | 12/2004 | Naasani |
| 2004/0248167 A1 | 12/2004 | Quake et al. |
| 2004/0266022 A1 | 12/2004 | Sundararajan et al. |
| 2004/0267568 A1 | 12/2004 | Chandler et al. |
| 2005/0004346 A1 | 1/2005 | Dziegiel et al. |
| 2005/0009002 A1 | 1/2005 | Chen et al. |

(56) References Cited

U.S. PATENT DOCUMENTS

| | | |
|---|---|---|
| 2005/0011764 A1 | 1/2005 | Berndt et al. |
| 2005/0014134 A1 | 1/2005 | West et al. |
| 2005/0032047 A1 | 2/2005 | Simmonds et al. |
| 2005/0043894 A1 | 2/2005 | Fernandez et al. |
| 2005/0059030 A1 | 3/2005 | Bao et al. |
| 2005/0071199 A1 | 3/2005 | Riff |
| 2005/0106257 A1 | 5/2005 | Albayrak |
| 2005/0112277 A1 | 5/2005 | Banerjee et al. |
| 2005/0120946 A1 | 6/2005 | Hines et al. |
| 2005/0128479 A1 | 6/2005 | Gilbert et al. |
| 2005/0164264 A1 | 7/2005 | Shipwash |
| 2005/0214536 A1 | 9/2005 | Schrier et al. |
| 2005/0221296 A1 | 10/2005 | Simmonds et al. |
| 2005/0227370 A1 | 10/2005 | Ramel et al. |
| 2005/0239118 A1 | 10/2005 | Goudsmit et al. |
| 2006/0008921 A1 | 1/2006 | Daniels et al. |
| 2006/0012784 A1 | 1/2006 | Ulmer |
| 2006/0014040 A1 | 1/2006 | Peng et al. |
| 2006/0019098 A1 | 1/2006 | Chan et al. |
| 2006/0029267 A1 | 2/2006 | Frost et al. |
| 2006/0046330 A1 | 3/2006 | Chen et al. |
| 2006/0063160 A1 | 3/2006 | West et al. |
| 2006/0068203 A1 | 3/2006 | Ying et al. |
| 2006/0078490 A1 | 4/2006 | Shih et al. |
| 2006/0105335 A1 | 5/2006 | Daehne et al. |
| 2006/0152372 A1 | 7/2006 | Stout |
| 2006/0169800 A1 | 8/2006 | Rosell |
| 2006/0173715 A1 | 8/2006 | Wang |
| 2006/0194030 A1 | 8/2006 | Barbera-Guillem |
| 2006/0265248 A1 | 11/2006 | Barnhart et al. |
| 2007/0020779 A1 | 1/2007 | Stavis et al. |
| 2007/0031283 A1 | 2/2007 | Davis et al. |
| 2007/0081920 A1 | 4/2007 | Murphy et al. |

FOREIGN PATENT DOCUMENTS

| | | |
|---|---|---|
| CA | 2518352 | 3/2005 |
| CN | 1948952 | 4/2007 |
| CN | 1964789 | 5/2007 |
| EP | 1315099 | 5/2003 |
| JP | 2002-271 | 1/2002 |
| JP | 2005-508493 | 3/2005 |
| WO | WO 99/19000 | 4/1999 |
| WO | WO 99/36564 | 7/1999 |
| WO | WO 99/64840 | 12/1999 |
| WO | WO 99/66318 | 12/1999 |
| WO | WO 00/13580 | 3/2000 |
| WO | WO 00/28598 | 5/2000 |
| WO | WO 00/70080 | 11/2000 |
| WO | WO 01/20533 | 3/2001 |
| WO | WO 01/89585 | 11/2001 |
| WO | WO 01/93754 | 12/2001 |
| WO | WO 02/04484 | 1/2002 |
| WO | WO 03/003015 | 1/2003 |
| WO | WO 2004/008550 | 1/2004 |
| WO | WO 2004/040319 | 5/2004 |
| WO | WO 2005/023923 | 3/2005 |
| WO | WO 2005/031802 | 4/2005 |
| WO | WO 2005/052996 | 6/2005 |
| WO | WO 2005/053649 | 6/2005 |
| WO | WO 2005/061095 | 7/2005 |
| WO | WO 2005/116632 | 12/2005 |
| WO | WO 2006/033732 | 3/2006 |
| WO | WO 2006/045004 | 4/2006 |
| WO | WO 2006/072306 | 7/2006 |
| WO | WO 2006/132953 | 12/2006 |
| WO | WO 2007/011622 | 1/2007 |
| WO | WO 2007/028271 | 3/2007 |
| WO | WO 2008/089155 | 7/2008 |
| WO | WO 2008/147382 | 12/2008 |
| WO | WO 2009/059404 | 5/2009 |

OTHER PUBLICATIONS

Alivisatos, A.P., Perspectives on the Physical Chemistry of Semiconductor Nanocrystals, Journal of Physical Chemistry, 1996, pp. 13226-13239, vol. 100, No. 31, American Chemical Society, USA.

Bakalova, Rumiana et al., Quantum dot-conjugated hybridization probes for preliminary screening of siRNA sequences, Journal of the American Chemical Society, Aug. 1, 2005, pp. 11328-11335, vol. 127, No. 32, American Chemical Society, USA.

Boldt, Klaus et al., Comparative Examination of the Stability of Semiconductor Quantum Dots in Various Biochemical Buffers, Journal of Physical Chemistry B, 2006, pp. 1959-1963, vol. 110, No. 5, American Chemical Society, USA.

Branch, Mary Ann et al., A Subspace, Interior, and Conjugate Gradient Method for Large-Scale Bound-Constrained Minimization Problems, SIAM J. Sci. Comput., Aug. 3, 1999, pp. 1-23, vol. 21, No. 1, Society for Industrial and Applied Mathematics.

Bruchez, Marcel Jr. et al., Semiconductor Nanocrystals as Fluorescent Biological Labels, Science, Sep. 25, 1998, pp. 2013-2015, vol. 281, American Association for the Advancement of Science, USA.

Burns, Mark A. et al., An Integrated Nanoliter Dna Analysis Device, Science, Oct. 16, 1998, pp. 484-487, vol. 282, No. 5388, American Association for the Advancement of Science, USA.

Chabinyc, Michael L. et al., An Integrated Fluorescence Detection System in Poly(dimethylsiloxane) for Microfluidic Applications, Analytical Chemistry, Sep. 15, 2001, pp. 4494-4498, vol. 73, No. 18, American Chemical Society, USA.

Chan, Eugene Y. et al., DNA Mapping Using Microfluidic Stretching and Single-Molecule Detection of Fluorescent Site-Specific Tags, Genome Research, 2004, pp. 1137-1146, vol. 14, Cold Spring Harbour Laboratory Press, USA.

Chan, Warren C.W. et al., Luminescent quantum dots for multiplexed biological detection and imaging, Current Opinion in Biotechnology, 2002, pp. 40-46, vol. 13, Elsevier Science Ltd.

Chan, Warren C.W. et al., Quantum Dot Bioconjugates for Ultrasensitive Nonisotopic Detection, Science, Sep. 25, 1998, pp. 2016-2018, vol. 281, American Association for the Advancement of Science, USA.

Chou, Hou-Pu et al., A microfabricated device for sizing and sorting DNA molecules, PNAS—Proceedings of the National Academy of Sciences of the United States of America, Jan. 1999, pp. 11-13, vol. 96, The National Academy of Sciences, USA.

Dabbousi, B.O. et al., (CdSe)ZnS Core-Shell Quantum Dots: Synthesis and Characterization of a Size Series of Highly Luminescent Nanocrystallites, Journal of Physical Chemistry B, 1997, pp. 9463-9475, vol. 101, No. 46, American Chemical Society, USA.

Duffy, D.C. et al., Rapid Prototyping of Microfulidic Systems in Poly(dimethylsiloxane), Analytical Chemistry, Dec. 1, 1998, pp. 4974-4984, vol. 70, No. 23, American Chemical Society, USA.

Eisenstein, Michael, Technology Feature: Protein Arrays—Growing pains, Losing the Label, an Apt Solution? & (Almost) No Assembly Required, Nature, Dec. 14, 2006, pp. 959-962, vol. 444, Nature Publishing Group, USA.

Fournier-Bidoz, Sebastien et al., Facile and Rapid One-Step Mass Preparation of Quantum-Dot Barcodes, Angewandte Chemie International Edition, 2008, pp. 5577-5581, vol. 47, No. 30, Wiley-VCH Verlag GmbH & Co. KGaA, Weinheim.

Fu, Anne Y. et al., A microfabricated fluorescence-activated cell sorter, Nature Biotechnology, Nov. 1999, pp. 1109-1111, vol. 17, Nature America Inc., USA.

Fu, Lung-Ming et al., Multiple injection techniques for microfluidic sample handling, Electrophoresis, 2003, pp. 3026-3032, vol. 24, Wiley-VCH Verlag GmbH & Co. KGaA, Weinheim.

Gao, Xiaohu et al., In vivo cancer targeting and imaging with semiconductor quantum dots, Nature Biotechnology, Jul. 18, 2004, pp. 969-976, vol. 22, No. 8, Nature Publishing Group, USA.

Gao, Xiaohu et al., Quantum Dot-Encoded Mesoporous Beads with High Brightness and Uniformity: Rapid Readout Using Flow Cytometry, Analytical Chemistry, Apr. 15, 2004, pp. 2406-2410, vol. 76, No. 8, American Chemical Society, USA.

(56) References Cited

OTHER PUBLICATIONS

Gao, Xiaohu et al., Quantum-dot nanocrystals for ultrasensitive biological labelling and mulitcolor optical encoding, Journal of Biomedical Optics, Oct. 2002, pp. 532-537, vol. 7, No. 4, SPIE.

Gaponik, Nikolai et al., Toward Encoding Combinatorial Libraries: Charge-Driven Microencapsulation of Semiconductor Nanocrystals Luminescing in the Visible and Near IR, Advanced Materials, Jun. 18, 2002, pp. 879-882, vol. 14, No. 12, Wiley-VCH Verlag GmbH, Weinheim.

Gershon, Diane, Technology Feature: DNA Microarrays—More than than gene expression, It's a Small World, Microassays Move Downstream & on the Hardware Front, Nature, Oct. 20, 2005, pp. 1195-1198, vol. 437, Nature Publishing Group, USA.

Goluch, E.D. et al., A bio-barcode assay for on-chip attomolar-sensitivity protein detection, Lab on a Chip, Aug. 15, 2006, pp. 1293-1299, vol. 6, The Royal Society of Chemistry.

Grumann, M. et al., Parallelization of Chip-Based Fluorescence Immuno-Assays with Quantum-Dot Labelled Beads, the 13th International Conference on Solid-State Sensors, Actuators and Microsystems, Jun. 2005, pp. 1114-1117, IEEE.

Han, Mingyong et al., Quantum-dot-tagged microbeads for multi-plexed optical coding of biomolecules, Nature Biotechnology, Jul. 2001, pp. 631-635, vol. 19, Nature Publishing Group, USA.

Hines, Margaret A. et al., Synthesis and Characterization of Strongly Luminescing ZnS-Capped CdSe Nanocrystals, Journal of Physical Chemistry B, 1996, pp. 468-471, vol. 100, No. 2, American Chemical Society, USA.

Kloepfer, Jeremiah A. et al., Photophysical Properties of Biologically Compatible CdSe Quantum Dot Structures, Journal of Physical Chemistry B, 2005, pp. 9996-10003, vol. 109, No. 20, American Chemical Society, USA.

Klostranec, Jesse M. et al., Convergence of Quantum Dot Barcodes with Microfluidics and Signal Processing for Multiplexed High-Throughput Infectious Disease Diagnostics, Nano Letters, Aug. 18, 2007, pp. 2812-2818, vol. 7, No. 9, American Chemical Society, USA.

Klostranec, Jesse M. et al., Quantum Dots in Biological and Biomedical Research: Recent Progress and Present Challenges, Advanced Materials, Aug. 4, 2006, pp. 1953-1964, vol. 18, No. 15, Wiley-VCH Verlag GmbH & Co. KGaA, Weinheim.

Li, Yougen et al., Multiplexed detection of pathogen DNA with DNA-based fluorescence nanobarcodes, Nature Biotechnology, Jul. 2005, pp. 885-889, vol. 23, No. 7, Nature Publishing Group, USA.

Liu, Wen-Tso et al., Microfluidic device as a new platform for immunofluorescent detection of viruses, Lab on a Chip, Oct. 4, 2005, pp. 1327-1330, vol. 5, The Royal Society of Chemistry.

Malamud, D. et al., Point Detection of Pathogens in Oral Samples, Adv Dent Res, Jun. 2005, pp. 12-16, vol. 18.

Marti et al., Design and characterization of two-dye and three-dye binary fluorescent probes for mRNA detection, Tetrahedron, Mar. 21, 2007, pp. 3591-3600, vol. 63, No. 17, Elsevier Science Publishers, Amsterdam, NL.

Mattoussi, H. et al., Luminescent Quantum Dot-Bioconjugates in Immunoassays, FRET, Biosensing, and Imaging Applications, JALA—Journal of the Association for Laboratory Automation, Feb. 2004, pp. 28-32, vol. 9, No. 1, The Association for Laboratory Automation, USA.

Medintz, Igor L. et al., Quantum dot bioconjugates for imaging, labelling and sensing, Nature Materials, Jun. 2005, pp. 435-446, vol. 4, Nature Publishing Group, USA.

More, Jorge J. et al., Computing a Trust Region Step, SIAM J. Sci. Stat. Comput., Sep. 1983, pp. 553-572, vol. 4, No. 3, Society for Industrial and Applied Mathematics.

Murray, C.B. et al., Synthesis and Characterization of Nearly Monodisperse CdE (E=S, Se, Te) Semiconductor Nanocrystallites, Journal of the American Chemical Society, 1993, pp. 8706-8715, vol. 115, No. 19, American Chemical Society, USA.

Neogi, A. et al., Enhanced luminescence efficiency from hydrogel microbead encapsulated quantum dots, Materials Research Society Symposium Proceedings, Jan. 1, 2007, pp. 202-207, vol. 959, Materials Research Society, USA.

Peng, Xiaogang et al., Epitaxial Growth of Highly Luminescent CdSe/CdS Core/Shell Nanocrystals with Photostability and Electronic Accessibility, Journal of the American Chemical Society, 1997, pp. 7019-7029, vol. 119, No. 30, American Chemical Society, USA.

Pregibon, Daniel C. et al., Multifunctional Encoded Particles for High-Throughput Biomolecule Analysis, Science, Mar. 9, 2007, pp. 1393-1396, vol. 315, American Association for the Advancement of Science, USA [downloaded on Mar. 9, 2009 from http://www.sciencemag.org].

Sathe, Tushar R. et al., Mesoporous Silica Beads Embedded With Semiconductor Quantum Dots and Iron Oxide Nanocrystals: Dual-Function Microcarriers for Optical Encoding and Magnetic Separation, Analytical Chemistry, Jul. 20, 2006, pp. 5627-5632, vol. 78, No. 16, American Chemical Society, USA.

Service, Robert F., DNA Analysis: Microchip Arrays Put DNA on the Spot, Science, Oct. 16, 1998, pp. 396-399, vol. 282, No. 5388, American Association for the Advancement of Science, USA [downloaded on Mar. 20, 2008 from http://www.sciencemag.org/cgi/content/full/282/5388/396].

Stavis, Samuel M. et al., Single molecule studies of quantum dot conjugates in a submicrometer fuidic channel, Lab on a Chip, Jan. 13, 2005, pp. 337-343, vol. 5, The Royal Society of Chemistry.

Sukhanova, A. et al., Nanocrystal-encoded fluorescent microbeads for proteomics: Antibody profiling and diagnostics of autoimmune diseases, Nano Letters, Aug. 2007, pp. 2322-2327, vol. 7, No. 8, American Chemical Society, USA.

Thomson, B. et al, Dispersion Copolymerization of Styrene and Divinylbenzee. II. Effect of Crosslinker on Particle Morphology, Journal of Applied Polymer Science, 1996, pp. 2009-2028, vol. 59, John Wiley & Sons, Inc.

Xu, Hongxia et al., Muliplexed SNP genotyping using the Qbead. TM. system: a quantum dot-encoded microsphere-based assay, Nucleic Acids Research, 2003, pp. 1-10, vol. 31, No. 8, Oxford University Press.

Xuan, Xiangchun et al., Focused electrophoretic motion and selected electrokinetic dispensing of particles of particles and cells in cross-microchannels, Electrophoresis, 2005, pp. 3552-3560, vol. 26, Wiley-VCH Verlag GmbH & co. KGaA, Weinheim.

Yun, Kwang-Seok et al., A microfluidic chip for measurement of biomolecules using a microbead-based quantum dot fluorescence assay, Measurement Science and Technology, 2006, pp. 3178-3183, vol. 17, IOP Publishing Ltd, UK.

Zaytseva, Natalya V. et al., Development of a microfluidic biosensor module for pathogen detection, Lab on a Chip, Jul. 6, 2005, pp. 805-811, vol. 5, The Royal Society of Chemistry.

International Search Report and Written Opinion from PCT/CA2009/001206 dated Jan. 19, 2010.

International Preliminary Report on Patentability from PCT/CA2009/001206 dated Nov. 26, 2010.

File History of U.S. Appl. No. 15/258,404.

Partical File History of U.S. Appl. No. 15/258,404 from Jun. 13, 2017 to Aug. 25, 2017.

SINGLE-USE HANDHELD DIAGNOSTIC TEST DEVICE, AND AN ASSOCIATED SYSTEM AND METHOD FOR TESTING BIOLOGICAL AND ENVIRONMENTAL TEST SAMPLES

CROSS REFERENCE TO RELATED APPLICATIONS

This is a continuation application of U.S. application Ser. No. 13/061,284 filed Feb. 28, 2011, which is a U.S. National Stage Application of International Application No. PCT/CA2009/001206 filed Aug. 31, 2009, which claims priority from U.S. Provisional Application No. 61/144,283 filed Jan. 13, 2009 and U.S. Provisional Application No. 61/093,036 filed Aug. 29, 2008. The entireties of all the above-listed applications are incorporated herein by reference.

FIELD OF THE INVENTION

The present invention relates generally to diagnostic test devices, and more particularly, to a single-use handheld diagnostic test device, and an associated system and method for testing biological and environmental test samples.

BACKGROUND OF THE INVENTION

Previously, rudimentary rapid tests may have been available on the market. Tests of this nature may have afforded a testing of only relatively basic parameters, such as typically may not have required any interpretation and/or a data management process in order to validate the test. More sophisticated and/or accurate rapid point-of-care tests may not heretofore have been possible, apart from at the hospital and/or in a core laboratory. This shortcoming of the prior art may have been due, in part, to the complexity of these kinds of diagnostic tests. At the same time, most prior art tests (whether simple or complex) may heretofore have required medical interpretation by qualified personnel.

Previously, in addition, the recordal of data in a computer for analysis and/or compilation in an electronic medical record (EMR) or healthcare repository may only have occurred in environments where there was access to a laboratory information system (LIS) or a hospital information system (HIS). That is, heretofore, automated recordal of results related to patient identification may have been, at best, very difficult and, often, impossible with simple prior art tests (e.g., lateral flow strips).

It is an object of an aspect of one preferred embodiment according to the present invention to provide a single-use handheld diagnostic test device, and/or an associated system and/or a method for testing biological and/or environmental test samples.

It is an object of an aspect of one preferred embodiment according to the present invention to provide disposable and/or reusable diagnostic test devices, systems and/or methods.

It is an object of an aspect of one preferred embodiment according to the present invention to reduce the number of complex features or requirements (e.g., IT infrastructure, connectivity, and/or professional interpretation of result) which may have been previously associated with substantially complete diagnostic test devices, systems and/or methods.

It is an object of an aspect of one preferred embodiment according to the present invention to provide substantially complete diagnostic test devices, systems and/or methods which may preferably be used with few or no complex features or requirements, such as, for example, IT infrastructure, connectivity, and/or professional interpretation of result.

It is an object of an aspect of one preferred embodiment according to the present invention to provide diagnostic test devices, systems and/or methods which afford a quality, level of result, and/or services which, heretofore, may only have been available in diagnostic tests performed in a core laboratory or hospital.

It is an object of an aspect of one preferred embodiment according to the present invention to provide diagnostic test devices, systems and/or methods which may preferably combine a disposable or reusable diagnostic test device with a conventional computing or networking electronic device.

It is an object of an aspect of one preferred embodiment according to the present invention to provide diagnostic test devices, systems and/or methods which may preferably combine a disposable or reusable diagnostic test device with a cellular telephone or laptop.

It is an object of an aspect of one preferred embodiment according to the present invention to provide diagnostic test devices, systems and/or methods which may preferably combine a disposable or reusable diagnostic test device with an identification system.

It is an object of an aspect of one preferred embodiment according to the present invention to provide diagnostic test devices, systems and/or methods which may preferably combine a disposable or reusable diagnostic test device with a biometric identification system.

It is an object of an aspect of one preferred embodiment according to the present invention to provide diagnostic test devices, systems and/or methods which may preferably be used by a patient and/or customer with minimal technical or clinical knowledge concerning the device technology or the interpretation of the test results.

It is an object of one preferred embodiment according to the invention to provide a device, system and/or method for use in biological and/or medical applications.

It is an object of the present invention to obviate or mitigate one or more of the aforementioned mentioned disadvantages associated with the prior art, and/or to achieve one or more of the aforementioned objects of the invention.

SUMMARY OF THE INVENTION

According to the invention, there is disclosed an electronic device and single-use handheld diagnostic test device system, for use with a biological and/or environmental test sample. The system includes an electronic device and a single-use handheld diagnostic test device. The test device is adapted to receive and operatively react the sample with one or more reagents. The test device includes a test connection element and at least one sensor. The sensor operatively detects test data from the sample after reaction with the reagents. The electronic device includes a mating electronic connection element, a processor, and a presentation element. The electronic connection element is operatively connected with the test connection element and electronically receives the test data from the test device. The processor operatively applies one or more algorithms to the test data to generate highly sensitive and accurate quantitative test results and presentation data based on the quantitative test results. The presentation element operatively presents to a user the presentation data based on the quantitative test results. The test device is adapted to test a single one said sample and is adapted for disposal, or for sterilization and re-use of the sensor and/or the test connection element, after the electronic device receives the test data.

According to an aspect of one preferred embodiment of the invention, the system also includes an identification element operative to identify the user. The identification element is provided in the form of a standalone identification component and/or integrally with the electronic device and/or the test device.

According to an aspect of one preferred embodiment of the invention, the identification element includes a biometric identification element. The biometric identification element preferably includes a fingerprint scanner, a retinal scanner, a microphone and voice recognition element, a camera and facial recognition element, and/or a genetic expression factor identification element.

According to an aspect of one preferred embodiment of the invention, the electronic device stores user identification data associated with the user and/or an owner of the electronic device. Preferably, the identification element automatically accesses the user identification data stored in the electronic device.

According to an aspect of one preferred embodiment of the invention, the system is adapted for use with an account associated with the user identification data. The system also includes a billing element operatively debiting the account in association with the generation of the quantitative test results.

According to an aspect of one preferred embodiment of the invention, the test device has onboard memory which electronically stores the test data and/or the algorithms. Preferably, but not necessarily, the processor of the electronic device operatively receives the algorithms from the test device via the test and electronic connection elements.

According to an aspect of one preferred embodiment of the invention, the processor operatively applies the algorithms to control the reaction of the sample with the reagents.

According to an aspect of one preferred embodiment of the invention, the presentation element includes a display element. Preferably, the algorithms generate the quantitative test results and/or the presentation data for presentation from the display element in the form of one or more visually presentable (a) textual data, (b) graphical data, and/or (c) colored indicator light data.

According to an aspect of one preferred embodiment of the invention, the test results are quantified as high, medium, and/or low results.

According to an aspect of one preferred embodiment of the invention, the electronic device has a battery. Preferably, the test connection element of the test device receives power, via the electronic connection element, from the battery.

According to an aspect of one preferred embodiment of the invention, the electronic device includes: (a) a test reader device; (b) a cellular telephone; (c) a mobile communications device; (d) a personal digital assistant; (e) a desktop computer; (f) a laptop computer; (g) a navigation device; (h) a digital audio player; (i) a camera; (j) a gaming device; (k) a television; and/or (l) a radio.

According to an aspect of one preferred embodiment of the invention, the electronic device includes a networking electronic device. Preferably, the networking electronic device automatically transmits the test data, the quantitative test results and/or the presentation data for recordal in one or more remote laboratory and/or hospital information systems.

According to an aspect of one preferred embodiment of the invention, the presentation data presented to the user includes treatment and follow-up suggestion data based on the test results.

According to the invention, there is also disclosed a single-use handheld diagnostic test device. The test device is preferably for use with an electronic device which has an electronic connection element, a presentation element, and a processor for operative application of one or more algorithms. The test device is adapted to receive and operatively react a biological and/or environmental test sample with one or more reagents. The test device includes at least one sensor and a mating test connection element. The sensor operatively detects test data from the sample after reaction with the reagents. The test connection element is operatively connected with, and electronically transmits the test data to the electronic device via, the electronic connection element. As such, the test device enables the processor to operatively apply the algorithms to the test data for generation of highly sensitive and accurate quantitative test results and presentation data based on the quantitative test results, and the presentation element to operatively present to a user the presentation data based on the quantitative test results. The test device is adapted to test a single one said sample. The test device is adapted for disposal, or for sterilization and re-use of the sensor and/or the test connection element, after the electronic transmission of the test data to the electronic device.

According to an aspect of one preferred embodiment of the invention, the test device also includes an identification element operative to identify the user. The identification element is provided in the form of a standalone identification component and/or integrally with the sensor and/or the test connection element.

According to an aspect of one preferred embodiment of the invention, the identification element includes a biometric identification element. The biometric identification element preferably includes a fingerprint scanner, a retinal scanner, a microphone and voice recognition element, a camera and facial recognition element, and/or a genetic expression factor identification element.

According to an aspect of one preferred embodiment of the invention, the test device is adapted for use with user identification data which is stored in the electronic device and is associated with the user and/or an owner of the electronic device. Preferably, the identification element automatically accesses the user identification data stored in the electronic device.

According to an aspect of one preferred embodiment of the invention, the test device is adapted for use with an account associated with the user identification data. Preferably, the test device also includes a billing element operatively debiting the account in association with the generation of the quantitative test results.

According to an aspect of one preferred embodiment of the invention, the test device also includes onboard memory which electronically stores the test data and/or the algorithms. Preferably, the test connection element electronically transmits the algorithms to the electronic connection element of the electronic device.

According to an aspect of one preferred embodiment of the invention, the electronic transmission of the algorithms by the test connection element to the electronic connection element of the electronic device is preferably such as to enable the processor to operatively apply the algorithms to control the reaction of the sample with the reagents.

According to an aspect of one preferred embodiment of the invention, the test device is adapted for use with a display element as the presentation element. The algorithms are adapted to generate the quantitative test results and/or the presentation data for presentation from the display element in the form of one or more visually presentable (a) textual data, (b) graphical data, and/or (c) colored indicator light data.

According to an aspect of one preferred embodiment of the invention, the algorithms are adapted to quantify the test results as high, medium, and/or low results.

According to an aspect of one preferred embodiment of the invention, the test device is adapted for use with a battery onboard the electronic device. The test connection element of the test device receives power, via the electronic connection element, from the battery.

According to an aspect of one preferred embodiment of the invention, the test device is adapted for use with one or more of following as the electronic device: (a) a test reader device; (b) a cellular telephone; (c) a mobile communications device; (d) a personal digital assistant; (e) a desktop computer; (f) a laptop computer; (g) a navigation device; (h) a digital audio player; (i) a camera; (j) a gaming device; (k) a television; and/or (l) a radio.

According to an aspect of one preferred embodiment of the invention, the test device is adapted for use with a networking electronic device as the electronic device. As such, the test device enables the networking electronic device to automatically transmit the test data, the quantitative test results and/or the presentation data for recordal in one or more remote laboratory and/or hospital information systems.

According to an aspect of one preferred embodiment of the invention, the device is adapted for use with presentation data presented to the user which includes treatment and follow-up suggestion data based on the test results.

According to the invention, there is also disclosed a method of testing a biological and/or environmental test sample. The method is for use with one or more reagents, an electronic device, and a single-use handheld diagnostic test device which is adapted to receive and test a single one said sample. The method includes the following steps: (a) a connection step; (b) a reaction step; (c) a sensing step after the connection step and the reaction step; (d) a data transmission step after the sensing step; (e) a processing step after the data transmission step; (f) a presentation step after the processing step; and/or (g) a disposal step after the data transmission step. In the connection step, a test connection element of the test device is connected with a mating electronic connection element of the electronic device. In the reaction step, the test device is used to react the sample with the reagents. In the sensing step, test data is detected from the sample using at least one sensor of the test device. In the data transmission step, the test data is electronically transmitted to the electronic connection element of the electronic device using the test connection element of the test device. In the processing step, one or more algorithms are applied to the test data using a processor of the electronic device to generate highly sensitive and accurate quantitative test results and presentation data based on the quantitative test results. In the presentation step, the presentation data based on the quantitative test results is presented to a user using a presentation element of the electronic device. In the disposal step, the test device is disposed of, or the sensor and/or the test connection element are sterilized and re-used.

According to an aspect of one preferred embodiment of the invention, the method also includes an identification step of using an identification element to identify the user. The identification element is provided in the form of a standalone identification component and/or integrally with the electronic device and/or the test device.

According to an aspect of one preferred embodiment of the invention, in the identification step, the identification element includes a biometric identification element and the user is biometrically identified. The biometric identification element preferably includes a fingerprint scanner, a retinal scanner, a microphone and voice recognition element, a camera and facial recognition element, and/or a genetic expression factor identification element.

According to an aspect of one preferred embodiment of the invention, the method also includes an ID storage step before the identification step. In the ID storage step, the electronic device is used to store user identification data associated with the user and/or an owner of the electronic device. In the identification step, the identification element automatically accesses the user identification data stored in the electronic device.

According to an aspect of one preferred embodiment of the invention, the method is adapted for use with an account associated with the user identification data. The method also includes a billing step after the identification step. In the billing step, the account is debited in association with the generation of the quantitative test results.

According to an aspect of one preferred embodiment of the invention, the method also includes a test device storage step before the data transmission step. In the test device storage step, the test data and/or the algorithms are electronically stored using onboard memory of the test device. The method also includes an algorithm transmission step before the processing step. In the algorithm transmission step, the algorithms are electronically transmitted to the processor, via the electronic connection element, using the test connection element of the test device.

According to an aspect of one preferred embodiment of the invention, the method also includes a reaction control step before completion of the reaction step. In the reaction control step, the processor is used to apply the algorithms to control the reaction of the sample with the reagents.

According to an aspect of one preferred embodiment of the invention, in the presentation step, the quantitative test results and/or the presentation data are presented from a display element of the presentation element. In the processing step, the algorithms generate the quantitative test results and/or the presentation data for presentation from the display element in the form of one or more visually presentable (a) textual data, (b) graphical data, and/or (c) colored indicator light data.

According to an aspect of one preferred embodiment of the invention, in the processing step, the test results are quantified as high, medium, and/or low results.

According to an aspect of one preferred embodiment of the invention, the method also includes a powering step before the data transmission step. In the powering step, the test connection element of the test device is used to receive, via the electronic connection element, power from a battery of the electronic device.

According to an aspect of one preferred embodiment of the invention, the method is adapted for use with one or more of following as the electronic device: (a) a test reader device; (b) a cellular telephone; (c) a mobile communications device; (d) a personal digital assistant; (e) a desktop computer; (f) a laptop computer; (g) a navigation device; (h) a digital audio player; (i) a camera; (j) a gaming device; (k) a television; and/or (l) a radio.

According to an aspect of one preferred embodiment of the invention, the method is adapted for use with a networking electronic device as the electronic device. The method also includes a network transmission step after the data transmission step. In the network transmission step, the networking electronic device is used to automatically transmit the test data, the quantitative test results and/or the presentation data for recordal in one or more remote laboratory and/or hospital information systems.

According to an aspect of one preferred embodiment of the invention, in the processing step, the presentation data generated by the algorithms includes treatment and follow-up suggestion data based on the test results. In the presentation step, the treatment and follow-up suggestion data is presented by the presentation element.

Other advantages, features and characteristics of the present invention, as well as methods of operation and functions of the related elements of the method, system and device, and the combination of steps, parts and economies of manufacture, will become more apparent upon consideration of the following detailed description and the appended claims with reference to the accompanying drawings, the latter of which are briefly described hereinbelow.

BRIEF DESCRIPTION OF THE DRAWINGS

The novel features which are believed to be characteristic of the system, device and method according to the present invention, as to their structure, organization, use, and method of operation, together with further objectives and advantages thereof, will be better understood from the following drawings in which presently preferred embodiments of the invention will now be illustrated by way of example. It is expressly understood, however, that the drawings are for the purpose of illustration and description only, and are not intended as a definition of the limits of the invention. In the accompanying drawings.

DETAILED DESCRIPTION OF THE PREFERRED EMBODIMENTS

Figure 1:
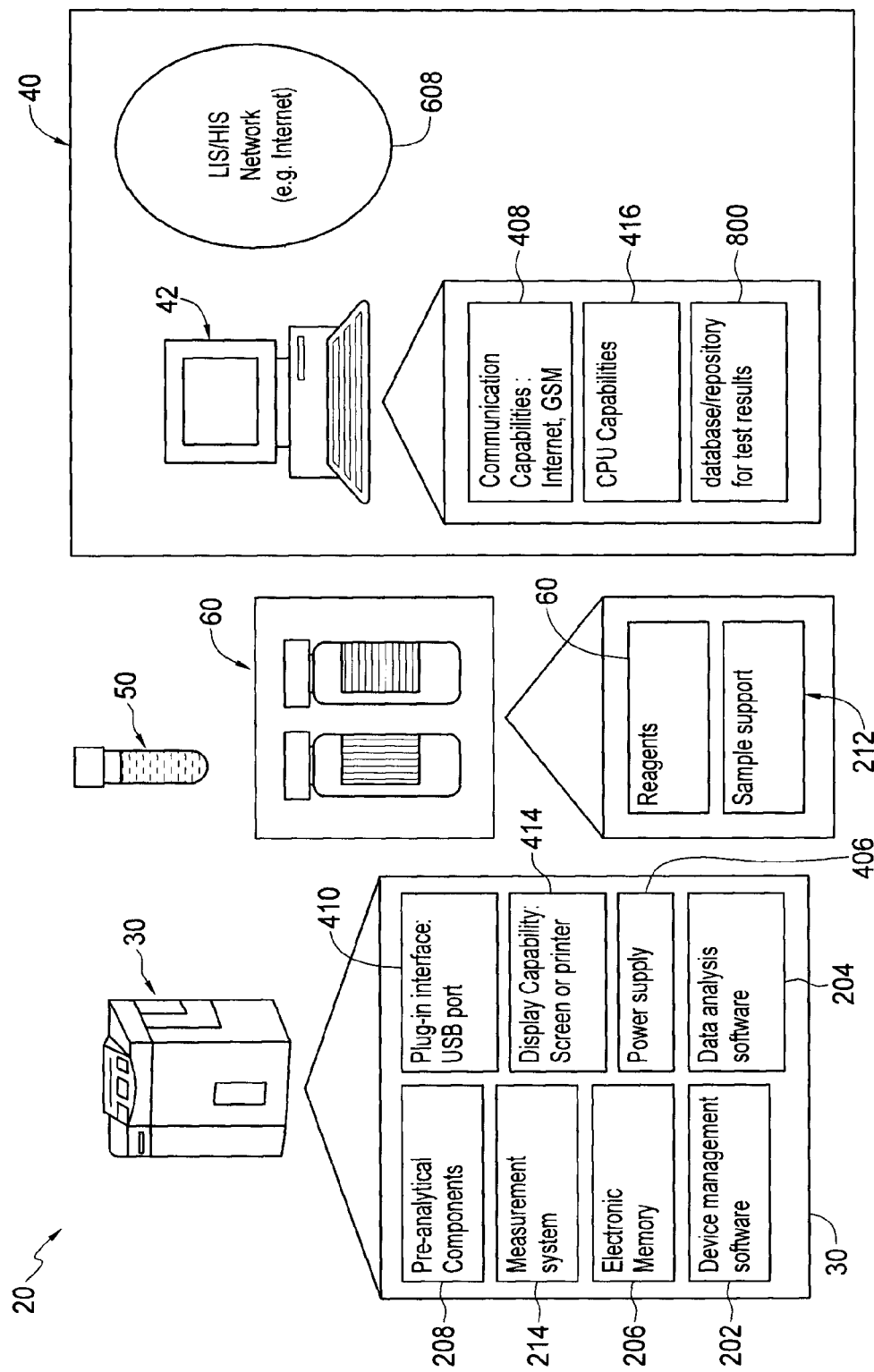
FIG. 1 is a schematic diagram of a prior art diagnostic system.

FIG. 1 shows an example of a prior art system 20 which includes a prior art diagnostic device 30 and prior art workstation and IT infrastructure 40. Such a prior art system 20 may have been for use with a biological test sample 50 and reagents 60 provided on a sample support 212 (i.e., a slide). As shown in FIG. 1, the prior art diagnostic device 30 is a desktop-sized device such as might have been previously used in a laboratory and/or hospital setting. The desktop-sized diagnostic devices 30 of the prior art may have included pre-analytical components 208, a measurement system 214, an electronic memory 206, device management software 202, a plug-in interface 410 (i.e., a USB port), a display capability 414 (i.e., a screen or printer), a power supply 406, and data analysis software 204 as shown in FIG. 1.

The prior art workstation and IT infrastructure 40 shown in FIG. 1 includes a desktop computer 42, such as may have been previously considered suitable for generation, recordal and display of highly sensitive and accurate quantitative test results. Persons having skill in the art may not generally have considered it feasible to create comparably sensitive and accurate test results outside of a laboratory or hospital setting. The desktop computer 42 may have provided CPU capabilities 416 and communication capabilities 408 (i.e., Internet, GSM). The prior art infrastructure 40 may also have included a laboratory and/or hospital information system (LIS/HIS) network 608 such as may have been, for example, accessible over the Internet. The prior art workstation and IT infrastructure 40 shown in FIG. 1 may have provided a database 800 and/or repository for recordal of the test results.

In FIGS. 2 to 8, there is shown a system 100 according to the present invention. The system 100 preferably includes an electronic device 400, an identification element 300, and a single-use handheld diagnostic test device 200 for use with a biological and/or environmental test sample 50.

Figure 8:
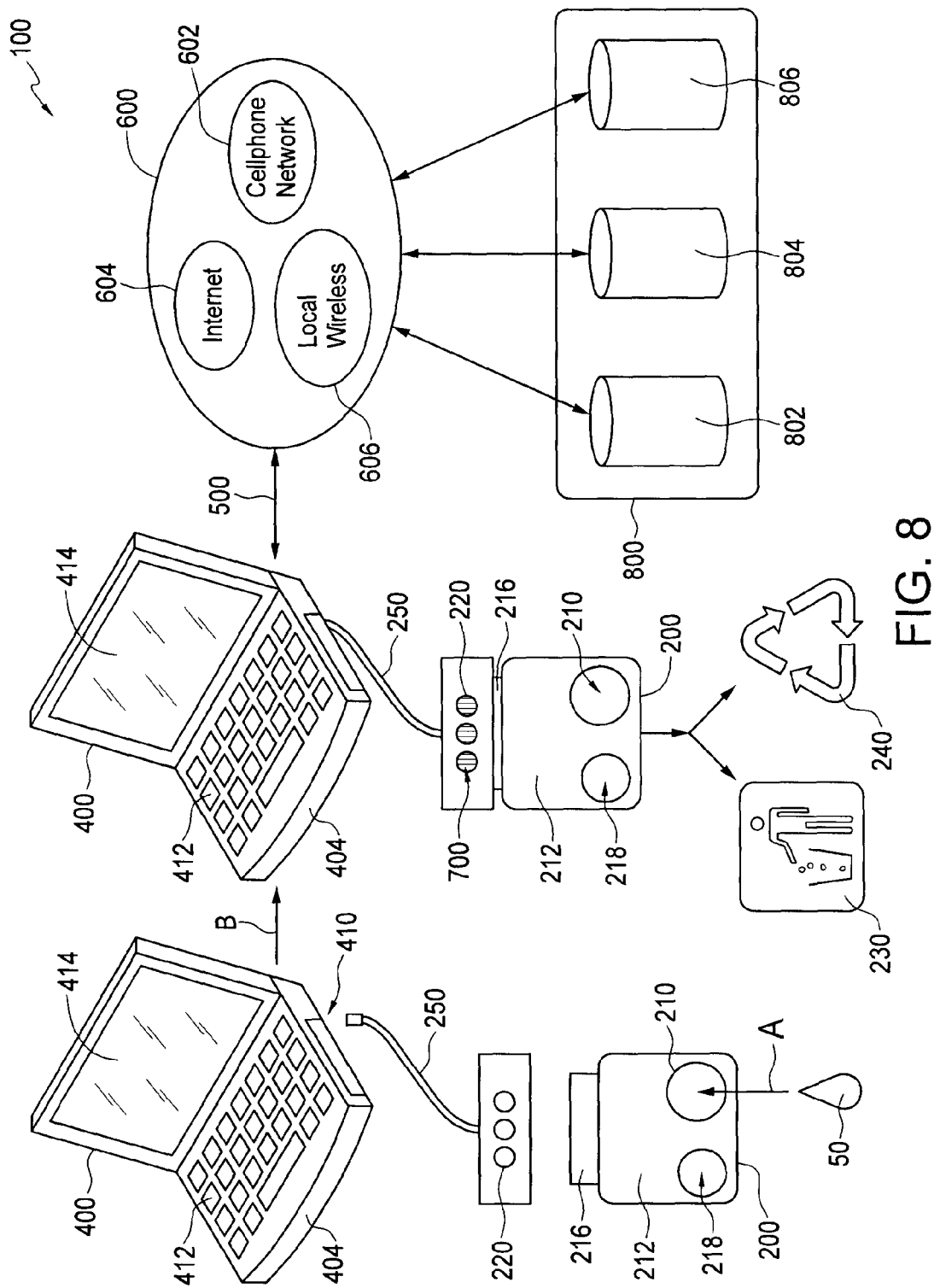
FIG. 8 is a schematic diagram of the system of FIG. 7, shown in use.

The test device 200 may preferably, according to the invention, be linked with more than one type and, more preferably, with a large range of electronic devices 400. The electronic device 400 may be a cellular telephone 402 (as shown in FIGS. 2 to 6) or a laptop computer 404 (as shown in FIG. 8). According to various other preferred embodiments of the invention, the electronic device 400 may take the form of a test reader device, a mobile communications device (e.g., a smart phone), a personal digital assistant, a pocket PC, a desktop computer, a navigation device, a digital audio player, a camera, a gaming device, a television, and/or a radio. According to some preferred embodiments of the invention, it may be suitable to utilize any electronic device 400 which provides a power source and/or the CPU capacity to run, analyze, record and/or transmit the test results.

Preferably, the test device 200 is for use with the electronic device 400, and is adapted to receive and operatively react the sample 50 with one or more reagents 60. The test device 200 preferably has onboard memory 206, a test connection element 216 and at least one sensor 214. The sensor 214 operatively detects test data (not shown) from the sample 50 after reaction with the reagents 60.

The test device 200 preferably provides components needed for performing the reaction, such as, all of the pre-analytical components 208, the reagents 60, and the sample support 212 (e.g., housing, slide, substrate) or platform for incubation.

The pre-analytical components 208 may preferably regroup the elements to mix the sample 50 with the reagents 60, preferably to identify the biological components targeted. In the case of lateral flow technology, one or more (or preferably most) of the pre-analytical components may be embedded inside the lateral flow strip.

The reagents 60 may preferably include reagents for the sample preparation. The reagents for the sample preparation may preferably include some (or preferably all) of the chemical components which may be required to lyse, extract and/or stabilize some specific biological components, so as to assist, facilitate and/or enable these biological components to be properly targeted. The reagents 60 may preferably be provided inside the test device 200. In some preferred embodiments according to the present invention, the reagents 60 may be stored in a small chamber or container inside the test device 200 or coated on a lateral flow strip. In some cases, one or more specific reagents 60 may be added manually by a user 90 (shown in FIG. 7) and/or by medical personnel.

The sample support 212 may preferably be provided as a housing (e.g., formed of plastic). Preferably, the sample support 212 may house and/or support some (or preferably all) of the components which are provided inside the test device 200.

The test device 200 preferably also provides the sensor (or measurement system) 214 for performing a measurement or detection, an interface (the test connection element 216) for data acquisition, and electronic data storage capacity within the onboard memory 206.

Depending on the technology used for detection, the sensor 214 may preferably, and by way of a non-limiting example, be optical in nature (e.g., relying on fluorescence or colorimetry) or electrical in nature (e.g., relying on impedance effects). Preferably, many different detection technologies may be capable of use within the test device 200 (and which may be capable of modification in function, in the discoveries made, and/or in the detection field), such as, for example and among other things, one or more of the following: lateral flow strip detection technologies; nano and/or micro cytometer detection technologies; impedance sensor detection technologies; dieletrophoresis detection technologies; micro PCR detection technologies; and/or electro peptide sensor technologies. The sensor 214 preferably receives a signal which is preferably transferred through data acquisition components so as to be sent, as is described in greater detail hereinbelow, to the electronic device 400. (In some alternate embodiments of the invention, optical fiber output or diode sensors may be used within the electronic device 400 as an excitation and/or optical sensor in place of, or in addition to, the sensors 214 of the test device 200. Preferably, however, the sensors 214 are provided as part of the test device 200.)

According to some preferred embodiments of the invention, the test connection element 216 may be provided as a separate or embedded component of the test device 200. The test connection element 216 may preferably link the test device 200 with the electronic device 400. Preferably, the test connection element 216 may assist, facilitate and enable a transfer of energy, data, and optical or electrical pulses.

The onboard memory 206 may preferably be provided within the test device 200. As is described in greater detail below, the onboard memory 206 may preferably be used to store data and software algorithms 202, 204 required to run the test—e.g., including the test method, the quality control data, the analysis process, the GUI interface instructions, and any other software applications or algorithms associated with the test—for data transfer or upload from the test device 200 to the electronic device 400. The onboard memory 206 may preferably store the test data. Stored test data may preferably be used later—e.g., if a patient wants to send the test device 200 to a central laboratory and/or a healthcare provider for further analysis. (In some embodiments of the invention, the onboard memory 206 may preferably also be associated with a CPU capability onboard the test device 200 to assist with or manage data transfer between the test device 200 and the electronic device 400.)

In some embodiments of the invention, the test device 200 may include a battery or power supply (not shown). This power supply may be provided, for example, in case the electronic device 400 is not capable of supporting the required or preferred power supply demands of the test device 200. That said, the electronic device 400 preferably includes a battery (or power supply) 406 of its own, which is sufficient to provide the test device 200 with an energy source.

The electronic device 400 preferably also includes an electronic connection element 410 and a processor (or CPU capability) 416. The processor 416 is for application of the software algorithms 202, 204 to process and/or analyze test data.

Figure 3:
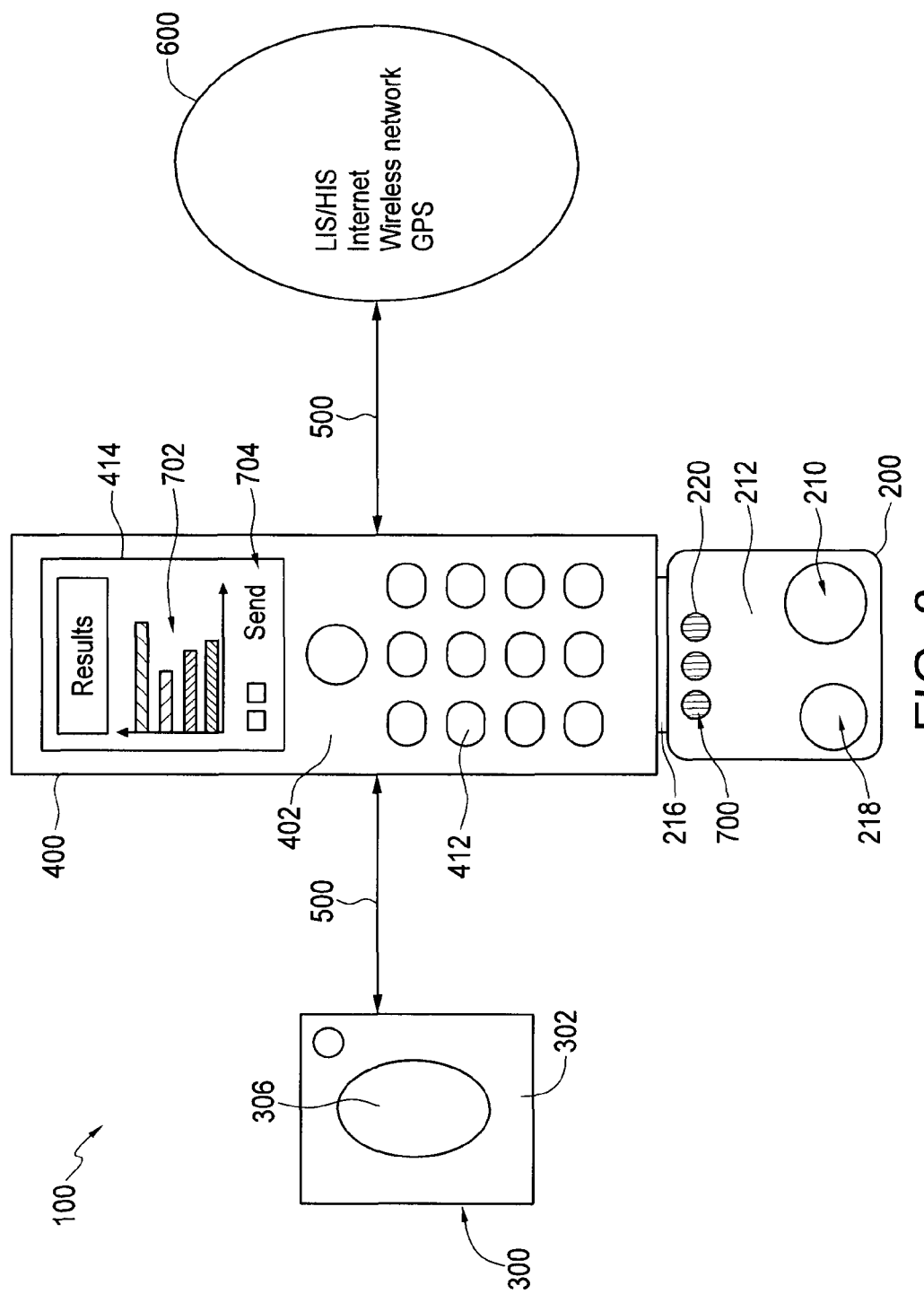
FIG. 3 is a schematic diagram of the system of FIG. 2, shown in use.
Figure 5:
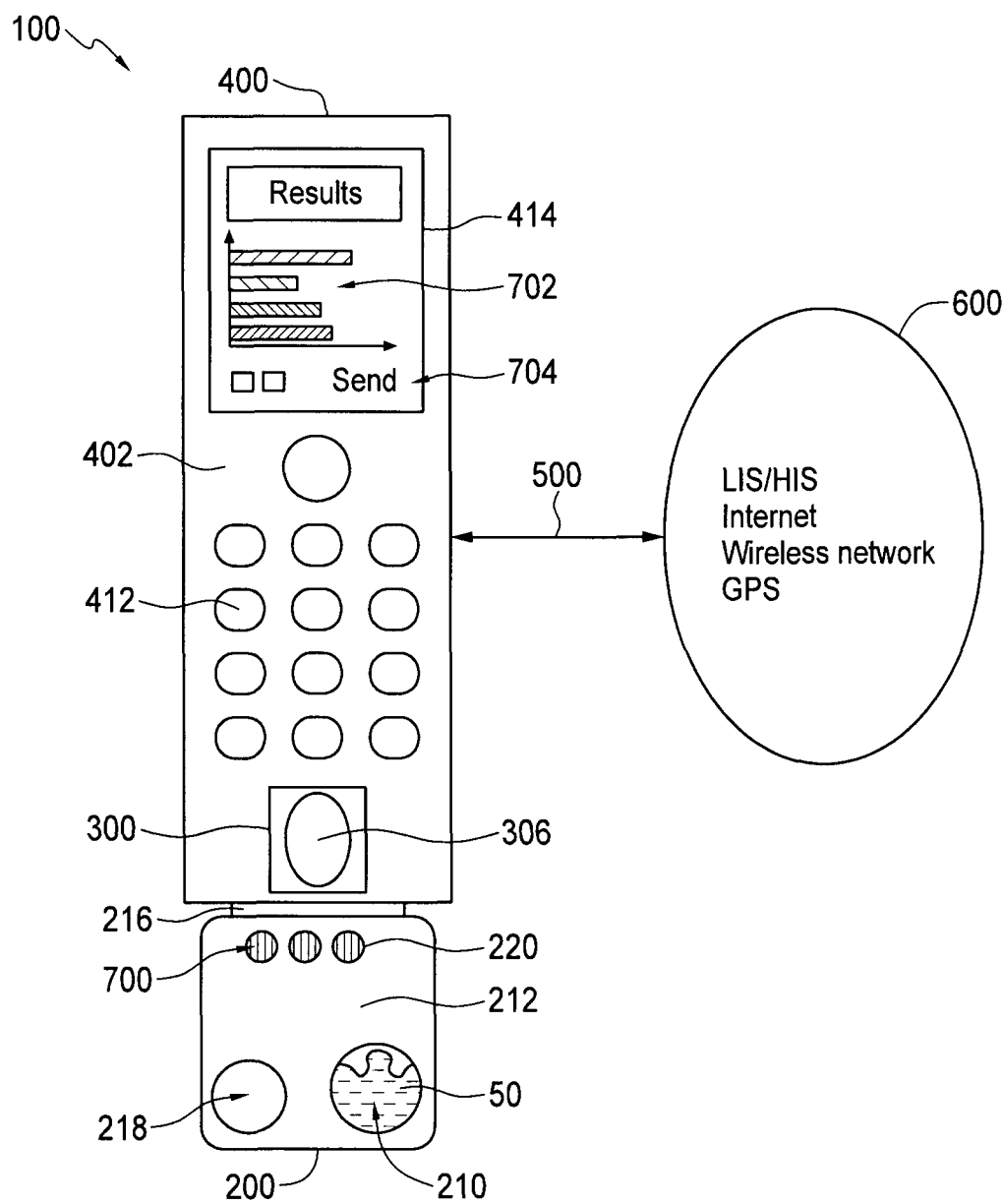
FIG. 5 is a schematic diagram of the system of FIG. 4, shown in use.

The electronic connection element 410 may preferably be a plug-in interface (e.g., a USB port). The electronic connection element 410 may preferably be provided as any kind of interfacing element suitable to transfer data and energy to the test device 200. The electronic connection element 410 and the test connection element 216 are operatively connected with one another in mating relation (as best seen in FIGS. 3 and 5). The interface between the test device 200 and the electronic device 400 may preferably utilize components which meet the connectivity requirements of the electronic device 400. Alternately or in addition, an interface component (not shown) may be provided which has a standard connectivity switch for the test device 200. Preferably, the test connection element 216 of the test device 200 receives power, via the electronic connection element 410, from the battery 406. The electronic connection element 410 is preferably capable of transferring the energy and/or power from the battery 406 to the test device 200. Preferably, the battery 406 affords a power supply capability to transfer energy sufficient to run the test device 200. Preferably, the test connection element 216 electronically transmits the test data to the electronic device 400 via the electronic connection element 410. In this manner, the electronic connection element 410 electronically receives the test data from the test device 200.

The processor 416 of the electronic device 400 may preferably provide enough processing capability to run the test device 200. Preferably, data included in the onboard memory 206 within the test device 200 may detail the minimum requirements, in terms of required processing capability, to run the test device 200. The processor 416 operatively applies one or more of the algorithms 202, 204 in managing the electronic device 400 and its interface with the test device 200. For example, the algorithms 202, 204 may include device management software 202 and data analysis software 204.

The device management software 202 may include graphical user interface (GUI) software, a framework application, and a data quality control application. The quality control application is preferably operative to check on the proper functioning of the test device 200 or to meet regulation requirements.

According to the invention, the GUI software may preferably assist, facilitate or enable display of some (or more preferably most or all) of the functionalities or results provided by the system 100. The GUI software may also preferably provide for connectivity functionalities—e.g., to send or receive data from one or more databases 800 and/or a communication system 600 via the electronic device 400. The GUI software may preferably be run, for example, inside a browser (e.g., an Internet browser) and/or through another GUI window.

The framework application may preferably help to regroup common software components, which may be used for some (or more preferably most or all) of the software applications or codes, in the operating system used between the electronic device 400 and the test device 200.

The data analysis software 204 may include test data processing applications and diagnostic applications. The diagnostic applications may preferably be accessed by the user 90, for example, to improve diagnostic analysis or to connect with an EMR repository. According to the invention, the user 90 or a patient may preferably also be able to download updates or new applications from a remote database or website.

The test data processing applications may preferably include algorithms to analyze the test data, and a data transfer protocol to enable the electronic device 400 to communicate with or download data from the test device 200. According to some embodiments of the invention, the processor 416 may also operatively apply the test data processing applications to control the reaction of the sample 50 with the reagents 60. Accordingly, by the aforesaid transmission of the test data processing applications and the test data, the test device 200 enables the processor 416 to, among other things, control the reaction of the sample 50 with the reagents 60. The testing of the sample 50 by the test device 200 may be directly initiated by the user 90 by controlling a dedicated button or a context dependent programmable button or key on the electronic device 400.

Thereafter, the processor 416 operatively receives the test data, and applies the test data processing applications to the test data to generate highly sensitive and accurate quantitative test results and/or presentation data based on the quantitative test data. In so doing, according to some preferred embodiments of the invention, the test results may be quantified as high, medium, and/or low results (e.g., a low intensity of infection result). Perhaps notably, the "highly sensitive and accurate quantitative test results" which are generated according to the present invention have comparable accuracy and sensitivity with those which have been previously quantified in a laboratory or hospital setting. Advantageously, therefore and due in part to the portability inherent in the handheld test device 200 and the electronic device 400, the present invention enables the generation of highly sensitive and accurate quantitative test results outside of such laboratory and hospital settings.

It may also be worthwhile to note that the presentation data presented to the user 90 may preferably include treatment and follow-up suggestion data based on the test results. The test device 200 is preferably adapted for use with, and to aid in the generation of, such presentation data. The treatment and follow-up suggestion data is preferably determined with reference to one or more of the algorithms 202, 204 stored onboard the electronic device 400 or the test device 200, or in one of the remote databases 800.

Preferably, the onboard memory 206 of the test device 200 electronically stores the test data and one or more of the algorithms 202, 204. Preferably, the test connection element 216 of the test device 200 electronically transmits such algorithms 202, 204 to the electronic connection element 410 of the electronic device 400. In this manner, the processor 416 operatively receives such algorithms 202, 204 from the test device 200 via the test and electronic connection elements, 216 and 410 respectively.

The electronic device 400 preferably also provides a presentation element 414, and further connectivity components. As shown in FIGS. 2 to 8, the presentation element 414 preferably includes a display element which has a display capability (e.g., a display screen and/or a printer) and/or which offers a graphical user interface (or GUI). Preferably, the algorithms 202, 204 generate the quantitative test results and/or the presentation data for presentation by the electronic device 400 in the form of visually and/or audibly presentable data. Audibly presentable data may take the form of a verbal, musical, tonal and/or other alert sounds. As women, children and men may be thought to have differing sensitivities from each other to some types of sounds, it may be preferable (according to some embodiments of the invention) to adapt the audibly presentable data to be only audible to one or more intended segments of listeners.

Visually presentable data may take the form of text, graphics and/or colored indicator lights. FIGS. 3 and 5-7 illustrate one form of visually presentable data which is contemplated according to the present invention, namely, visually presentable graphical data 702. Among other things, graphical data may include charts and other comparative visual representations of the quantitative test results. By way of example, and among other things, visually and/or audibly presentable data may also include descriptive and/or numerical data. Exemplary types of descriptive data may include the presentation data (e.g., the treatment and follow-up suggestion data) and/or intensity information. Intensity data may be shown in textual and/or graphical format. Exemplary types of numerical data may include the quantitative test results. Other visually presentable data may include textual data, and/or colored indicator light data. Preferably, the display screen enables display of the quantitative test results and/or presentation data, and management of the system 100. (In some embodiments of the invention, the printer or other kinds of output systems are used for visualization or presentation.) The presentation element 414 operatively presents the quantitative test results and/or the presentation data to the user 90. Accordingly, by the aforesaid transmission of the test data processing applications and the test data, the test device 200 also enables generation and presentation of the test results and the presentation data by the processor 416 and the presentation element 414.

Figure 2:
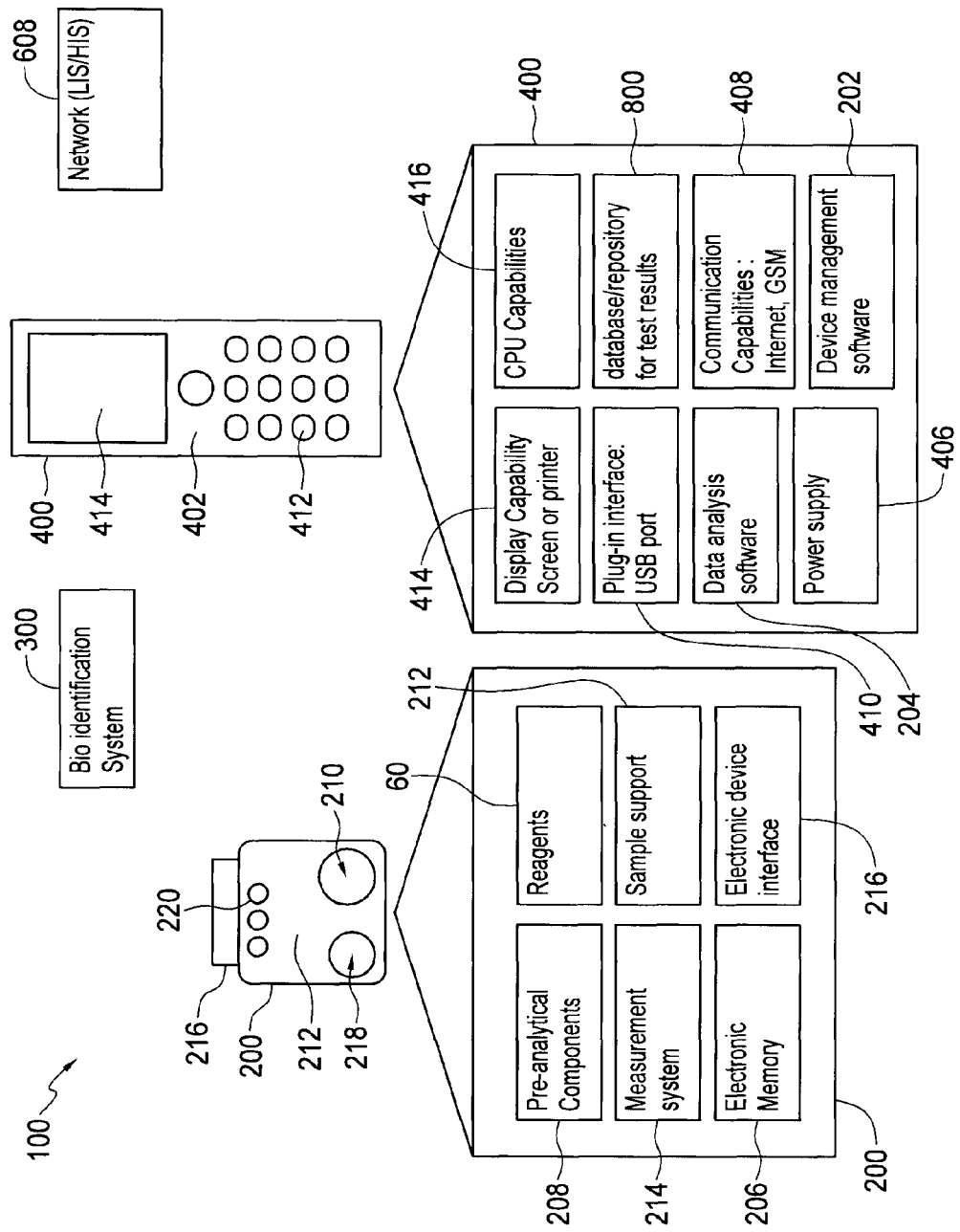
FIG. 2 is an exploded schematic diagram of a system according to a first preferred embodiment of the invention.
Figure 4:
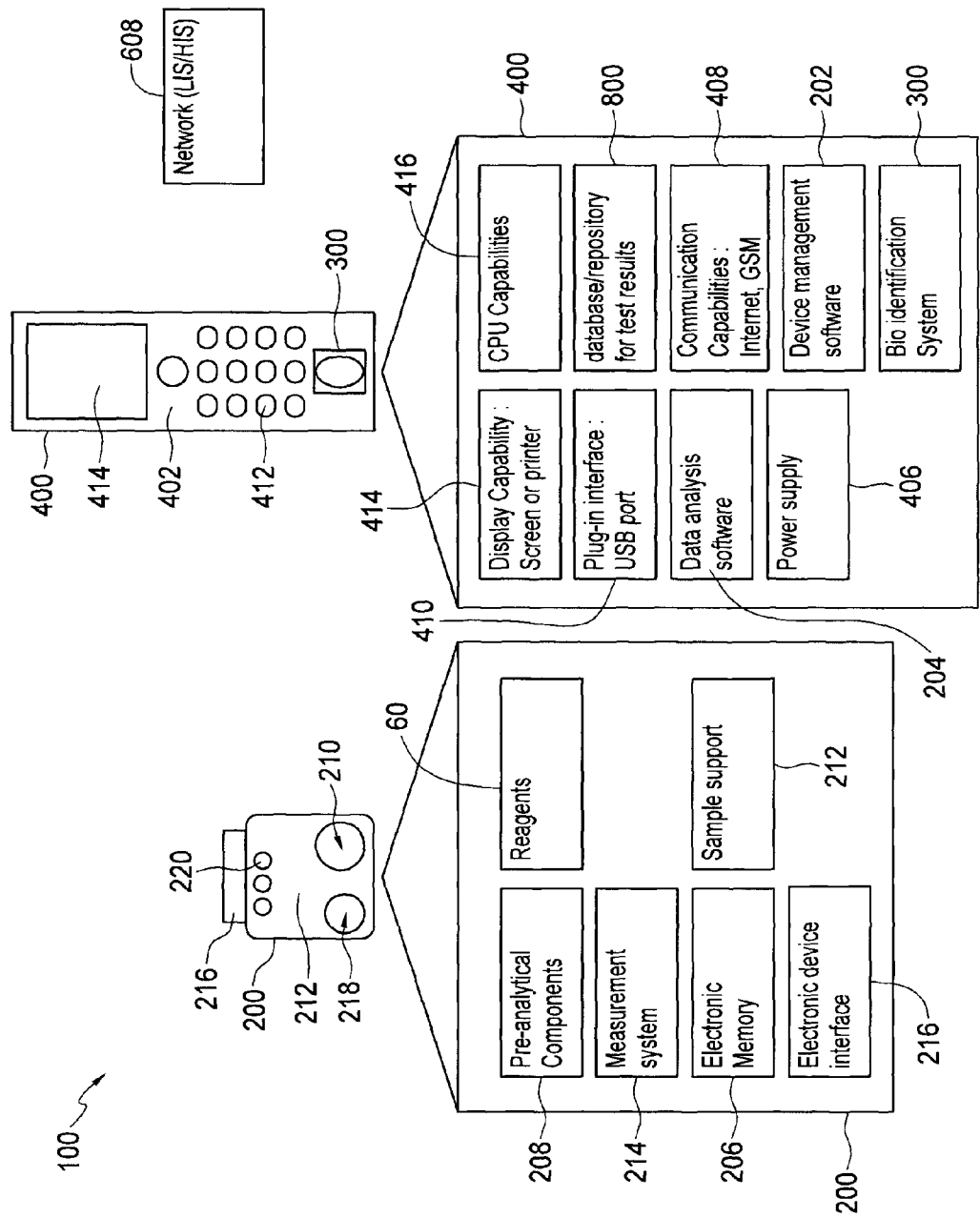
FIG. 4 is an exploded schematic diagram of a system according to a second preferred embodiment of the invention.
Figure 7:
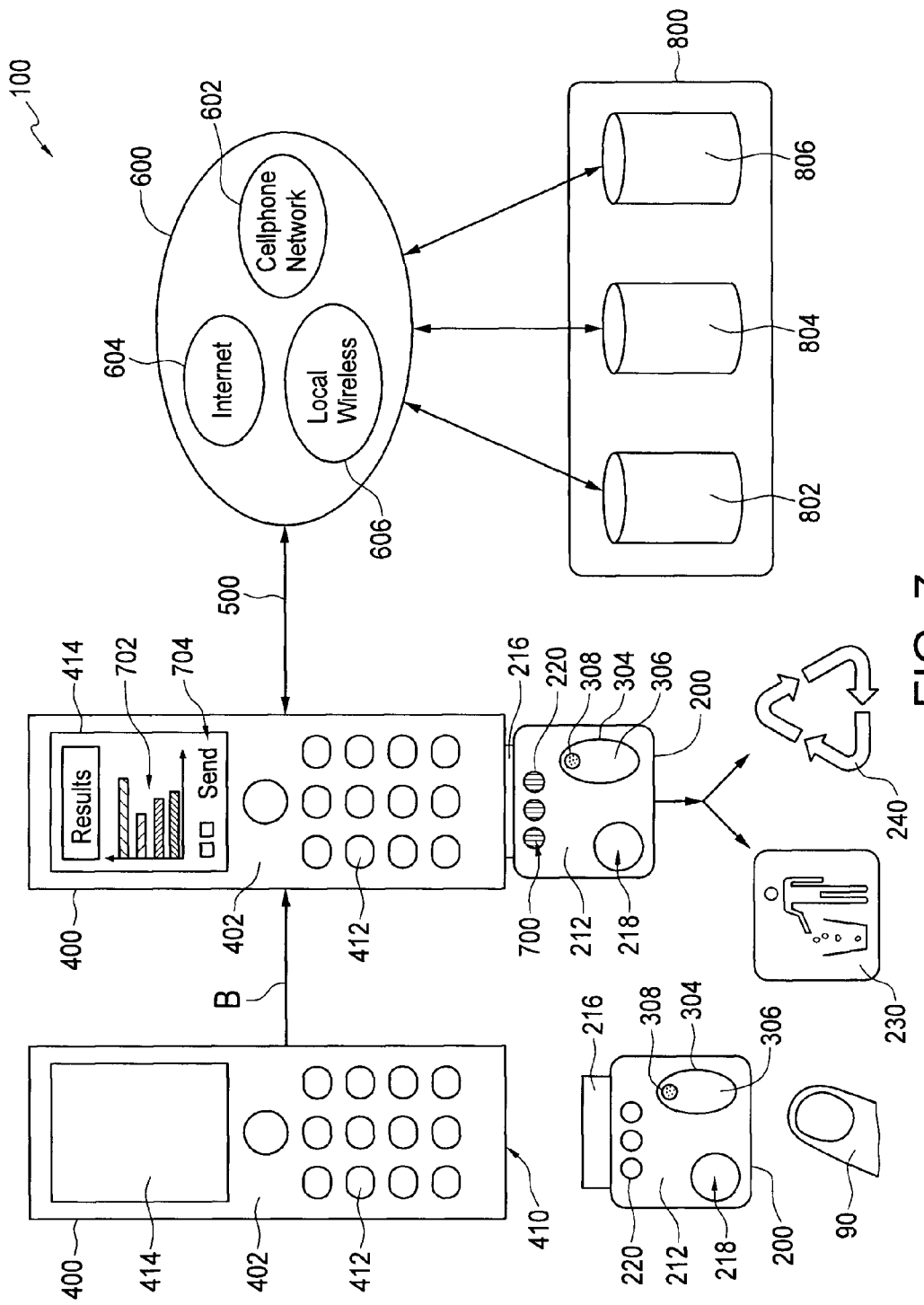
FIG. 7 is an exploded schematic diagram of a system according to a fourth preferred embodiment of the invention.

The identification element 300 is operative to identify the user 90. The identification element 300 may be provided in the form of a standalone identification component 302 (as shown in FIGS. 2 and 3) or integrally with the electronic device 400 (as best seen in FIGS. 4 and 5) or the test device 200 (as shown in FIG. 7)—e.g., with the sample support 212, the sensor 214 and/or the test connection element 216. That is, the identification element 300 may be provided integrally or in association with the electronic device 400. Alternately, the identification element 300 may also or instead be provided apart from the electronic device 400 and connected to it via a wireless or USB connection (as best seen in FIG. 3). In some cases, the identification element 300 may be embedded inside the test device 200—e.g., to provide a better and/or higher tracking ID security system. As shown in FIG. 7, the identification element 300 may preferably be included as part of the test device 200. For cost reasons, however, it may be more economical to provide the identification element 300 (and any related bio-recognition system) as part of the electronic device 300 or in the form of the aforesaid standalone identification component 302.

Preferably, the identification element 300 may include a biometric identification element. For example, the biometric identification element may be a fingerprint scanner 306 (as shown in FIGS. 2-5 and 7), a retinal scanner, a microphone and voice recognition element, a camera and facial recognition element, and/or a biological sample extractor 308 (or genetic expression factor identification element 308, as shown in FIG. 7). Of course, other present and/or future bio-recognition systems which may be available may also be suitable for use in accordance with the present invention.

The electronic device 400 stores user identification data (not shown) associated with the user 90 and/or an owner of the electronic device 400. Preferably, the identification element 300 automatically accesses the user identification data stored in the electronic device 400 in the process of identifying the user 90.

According to some preferred embodiments of the invention, the system 100 is adapted for use with an account (not shown) associated with the user identification data. The system 100 also includes a billing element (not shown) which operatively debits the account in association with the generation of the quantitative test results 702.

The electronic device 400 is preferably a networking electronic device and is provided with a communication subsystem 408 to afford connectivity and/or communications (e.g., network connection, GSM, satellite connection, Internet) capabilities. As shown in FIGS. 3 and 5-8, the communication subsystem 408 networks with an external communications system 600 which may include satellite networks (e.g., GPS networks), terrestrial wireless networks (e.g., a cellular telephone network 602, a local wireless network 606), the Internet 604, and laboratory and/or hospital information systems (LIS/HIS networks) 608. The electronic device 400 may preferably be in wireless (and/or wired) communication with at least one communication system 600.

The communication subsystem 408 which is provided may preferably depend on the type or version of the electronic device 400 used in the system 100. In the case of a cellular telephone 402, for example, the system 100 may preferably use its wireless capability to transmit data via the cellular telephone network 602 to one of the remote databases 800. In the case of the laptop 404 shown in FIG. 8 (or the pocket PC), the communication subsystem 408 may preferably be an intranet connection, or a wired or wireless Internet 604 connection.

The electronic device 400 may preferably also have the ability to connect quickly and easily to the LIS/HIS networks 608 via, for example, the local wireless network 606 (e.g., a Bluetooth network) and/or a USB cable. Preferably, the electronic device 400 automatically transmits the test data, the quantitative test results and/or the presentation data for recordal in one or more remote LIS/HIS networks 608. Additionally, transmission of the test data, the quantitative test results or the presentation data by the electronic device 400, via the communication subsystem 408 over the communication system 600, may be initiated directly and/or indirectly by the user 90 by controlling a dedicated button or a context dependent programmable button or key. Preferably, the electronic device 400 may be able to record the test results or the biometrics information related to each test. The remote databases 800 may also be used for various tests or patients and are preferably linkable with the data stored on the electronic device 400.

Figure 6:
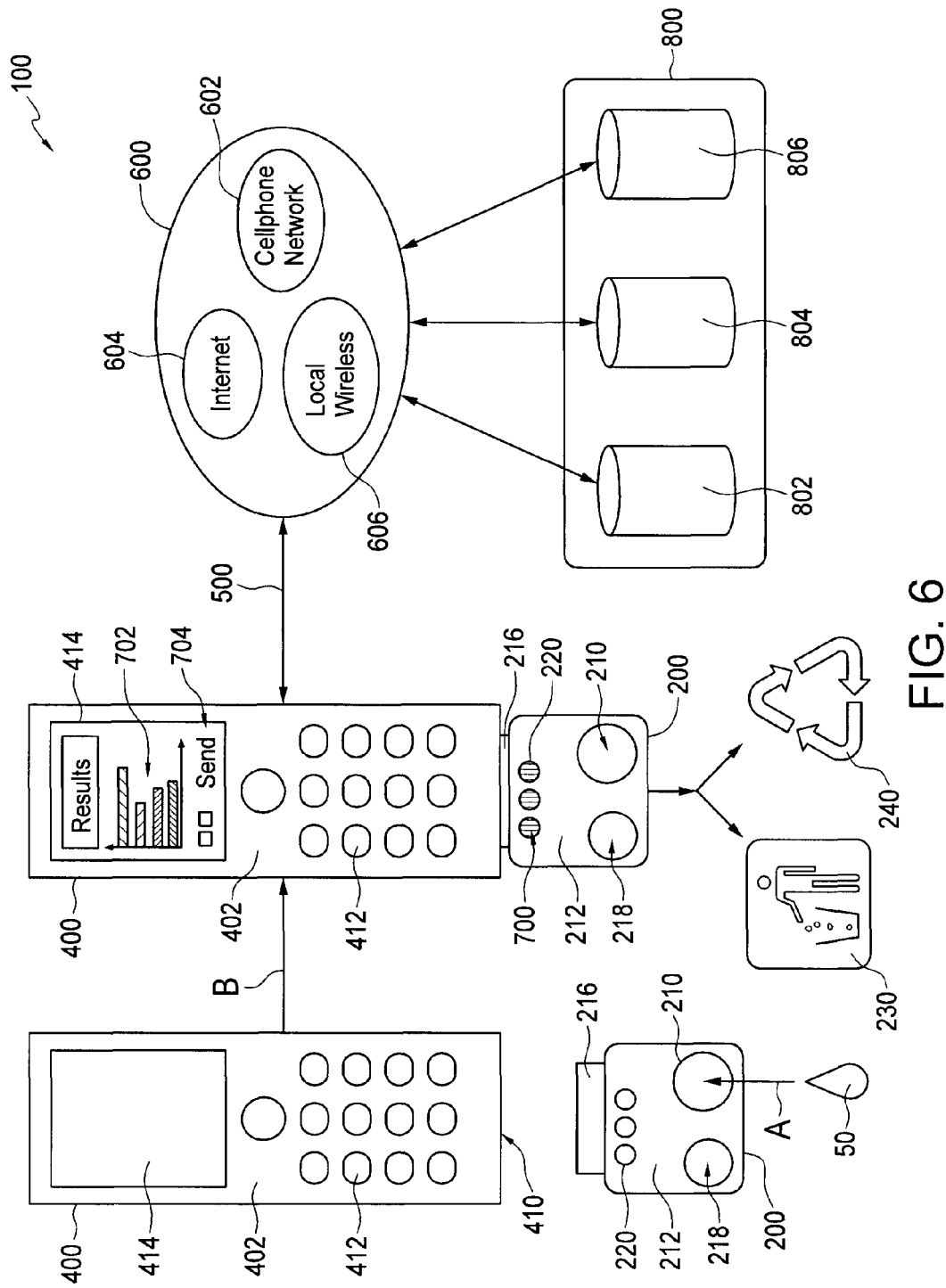
FIG. 6 is a schematic diagram of a system according to a third preferred embodiment of the invention, shown in use.

As shown in FIGS. 6 to 8, various databases 800 may interface with the communications system 600, preferably including, waste treatment services databases 802, software applications databases 804 (e.g., clinical software applications, database software applications, download portals, quality control central databases), and various test result databases 806 (e.g., healthcare providers database, governmental agency databases, military department databases). Notably, the databases 800 may include, without limitation, epidemiologic databases, UN and major/international healthcare institution databases, healthcare and emergency infrastructure databases, education and economic databases, news databases, demographic databases, communication and military infrastructure databases, and weather and topographic databases. The databases 800 may preferably serve as an additional repository for the test results (test result databases 806), as a source for test processing algorithms and software applications (the software applications databases 804), and/or as a resource for coordination of waste treatment or other services (e.g., the waste treatment services databases 802).

Communication functions, including data and voice communications, may be performed through the communication subsystem 408. The communication subsystem 408 preferably acts as both a receiving element and a transmitting element. The communication subsystem 408 may receive messages from and send messages via (e.g., USB, wireless) communication signals 500 to the communication system 600. The electronic device 400 may send and receive communication signals over the communication system 600. Some of the subsystems of the electronic device 400 may perform communication-related functions, and some may provide "resident" or on-device functions. By way of example, the display element may be used for both functions.

The processor 416 may also interact with additional subsystems of the electronic device 400, such as a random access memory (RAM), a flash memory, other presentation elements (including colored indicator lights and a speaker), a short-range communications system, and a GPS subsystem. Operating system software for the standard functions of the electronic device 400 used by the processor 416 may typically be stored in a persistent store such as the flash memory. Those skilled in the art will appreciate that the operating system, specific device applications, or parts thereof, may be temporarily loaded into a volatile store, such as the RAM, for processing by processor 416.

The test device 200 is adapted to test a single one said sample 50 and is adapted for disposal or for sterilization and re-use (e.g., of the sensor 214 and/or the test connection element 216) after the electronic device 400 receives the test data. That is, the test device 200 may preferably be provided as a fully disposable or consumable test device, or as a partially reusable test device.

In the fully disposable or consumable version of the test device 200, all of the components needed for the test are included and many may be consumed during the test or may not endure beyond the transmission of the test data. At the end of the test, this test device 200 is adapted to be discarded or sent to healthcare institutions or corporations for analysis or waste treatment. The fully disposable or consumable version of the test device 200 may preferably be adapted for use directly by the patient (e.g., to test herself).

In the partially reusable version of the test device 200, some components may preferably be reusable by the patient or doctor in subsequent tests. Some of the components which may preferably be capable of reuse may include, without limitation, the sensors 214 and/or the test connection element 216. Some of the components which may preferably be provided as consumables may include the pre-analytical components 208, the reagents 60, and/or the onboard memory 206. The partially reusable version of the test device 200 may preferably find particularly advantageous utility when a patient seeks and/or requires recurrent testing (e.g., for diabetes, cardiac diseases, HIV) or when a patient seeks or needs to be monitored, on an ongoing basis, in association with a specific condition or treatment (e.g., thrombosis, chemotherapy). Another utility for the partially reusable version of the test device 200 may include contemplated uses in a small medical dispensary, in clinics, in doctors' offices, or in other locales where, for example, a small number of tests may be performed per day. In this version of the test device 200, the ongoing costs associated with performing any necessary tests may be restricted, in part, to the price of the consumables—such as, for example, the reagents, the pre-analytical components, and in some cases, a few additional components (e.g., the memory).

Ideally, the above-described combination of the test device 200, the identification element 300, and the electronic device 400 may preferably allow a patient and/or healthcare provider to readily perform—preferably at their fingertips and/or in the palm of their hand—one or more diagnostic tests with substantially the same analytic capability as other substantially more unwieldy prior art high-tech diagnostic devices.

Preferably, and as aforesaid, some preferred embodiments of the invention may involve use of a mobile or cellular telephone 402 as the electronic device 400—i.e., in association with the test device 200. In other embodiments of the invention, such as that shown in FIG. 7, the test device 200 integrally includes the identification element 300. The identification element 300 shown in FIG. 7 includes a combined fingerprint scanner and biological sample extractor 304. Preferably, substantially contemporaneous with the user 90 putting his or her finger on the provided fingerprint scanner 306, the biological sample extractor 308 may preferably draw, by capillary action, a drop of blood therefrom, inter alia, as the sample 50 and for supplemental identification purposes. Preferably, in still further embodiments (and by way of a non-limiting example), the identification element 300 may be integrally included as part of the electronic device 400 by utilizing a camera (not shown) of the cellular telephone 402 to act as the biometric element.

As shown in FIG. 8, according to some embodiments of the invention, the test device 200 may also be connected with the laptop 404 via a USB port (as the electronic connection element 410) and/or via any other available port to provide data transfer and/or energy supply. Similarly, though not shown in the drawings, the test device 200 may be used with a desktop computer and/or a pocket PC according to the present invention. As in the case of the laptop 404 (discussed above), the test device 200 may also be connected with the desktop computer and/or pocket PC via a USB port (as the electronic connection element 410) and/or via any other available port to provide data transfer and/or energy supply.

With reference to the various embodiments of the system 100 which are shown in the drawings, it will be appreciated by one skilled in the art that, although some components, relations, processes and aspects of same are only discussed with reference to one or more specific drawings, same may be used and/or adapted for use in association with embodiments shown in other ones of the drawings.

Figure 9:
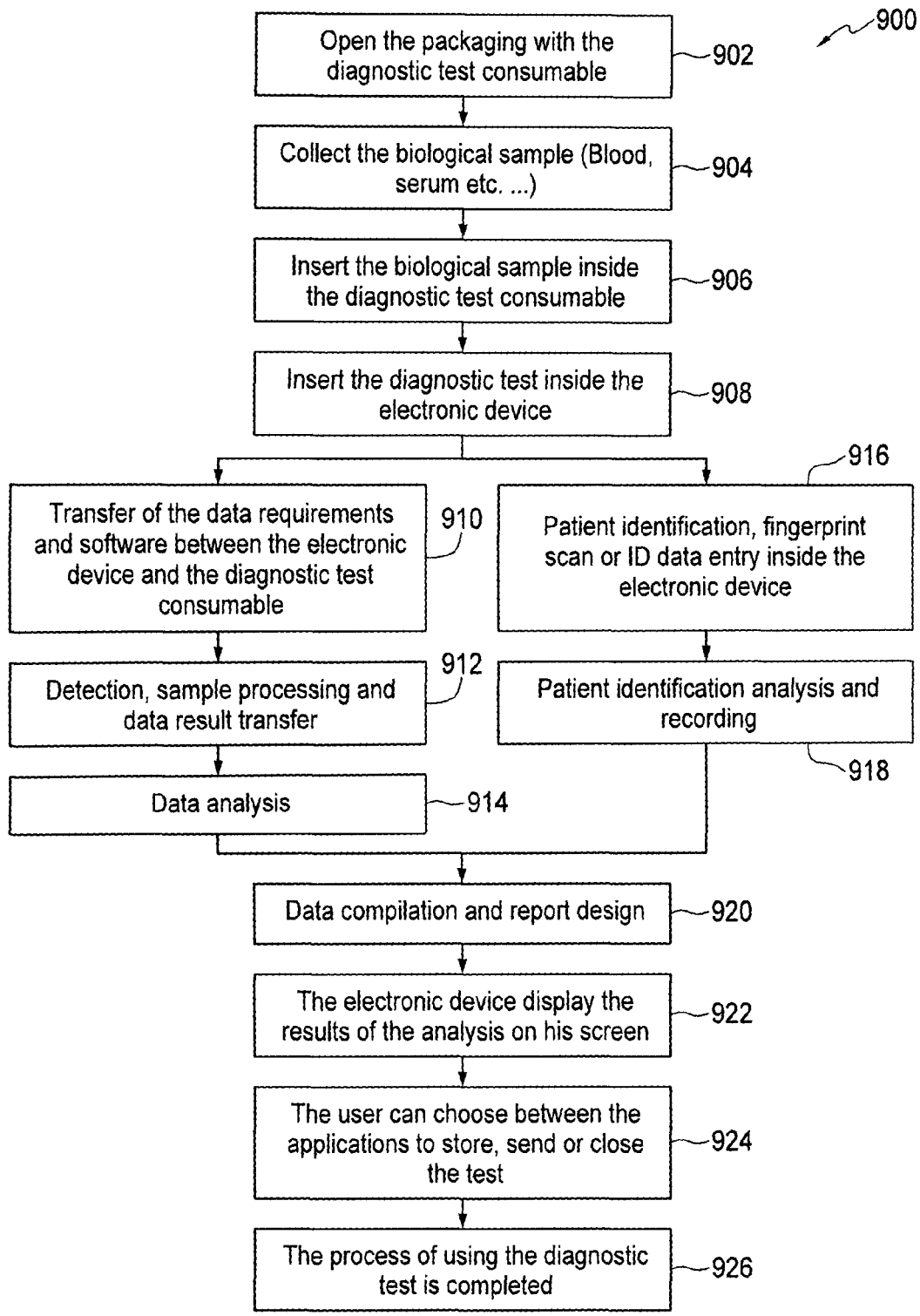
FIG. 9 is a flowchart of an illustrative method according to the invention.

FIG. 9 shows, schematically by way of overview, an associated method 900 of testing the sample 50, for use with the reagents 60, the electronic device 400, and the test device 200. The method 900 preferably includes the following steps, among others: a test device preparation step 902, a sample collection step 904, a sample loading step 906, a connection step 908, a test device storage step, an algorithm transmission step 910, a powering step, a reaction control step, a reaction step (see method step 912 in FIG. 9), a sensing step (see method step 912 in FIG. 9), a test device storage step, a data transmission step (see method step 912 in FIG. 9), a processing step 914, an ID storage step, an identification step 916, an ID analysis and recording step 918, a compilation and report design step 920, a presentation step 922, a network transmission step 924, a billing step, a use completion step 926, and/or a disposal step.

In the test device preparation step 902, the test device 200 is preferably removed from its packaging inside of a hermetically sealed plastic bag or a small plastic box. Such packaging is used to keep dry one or more of the reagents 60 and/or the test device 200. Next, a USB cable 250 or other connectivity interface element is preferably plugged into the test device 200. The USB cable 250 may be considered to be part of the test device 200, the electronic device 400, or a standalone component of the system 100.

As shown in FIGS. 2 to 8, the test device 200 (and the USB cable 250) may preferably be provided with process control indicator lights 220 to indicate process control data 700 concerning the reaction of the sample 50 with the reagents 60. In some exemplary embodiments, when three process control indicator lights 220 are alit, the reaction of the sample 50 with the reagents 60 has concluded and/or the test data has been transmitted to the electronic device 400. In any event, in FIGS. 6 to 8, arrow "B" indicates a diagnostic test processing step which is performed.

The sample 50 is collected in the sample collection step 904. In the sample loading step 906, the user 90 (e.g., a patient, nurse and/or doctor) may preferably load the sample 50 (e.g., a drop of blood), in a sample loading direction as indicated by arrow "A" in FIGS. 6 and 8, into a sample chamber 210 of the test device 200.

In the connection step 908, the test connection element 216 and the electronic connection element 410 are connected in mating relation, with the test device 200 plugged into the electronic device 400.

The test device storage step occurs before the data transmission step. In the test device storage step, the test data and/or the algorithms 202, 204 are electronically stored using the onboard memory 206 of the test device 200.

The algorithm transmission step 910 occurs before the processing step 914. In the algorithm transmission step 910, the test device 200 preferably transfers, to the electronic device 400, some data concerning use of the test device 200, or one or more algorithms 202, 204 to process or analyze test data using the electronic device 400. That is, in the algorithm transmission step 910, the algorithms 202, 204 are electronically transmitted to the processor 416, via the electronic connection element 410, using the test connection element 216 of the test device 200.

The powering step occurs before the data transmission step. In the powering step, the test connection element 216 of the test device 200 is used to receive, via the electronic connection element 410, power from the battery 406 of the electronic device 400.

The reaction control step occurs before completion of the reaction step. In the reaction control step, the processor 416 is used to apply one or more of the algorithms 202, 204 to control the reaction of the sample 50 with the reagents 60.

During the reaction step (see method step 912 in FIG. 9), the test device 200 is used to react the sample 50 with the reagents 60, and the electronic device 400 may preferably open a window and/or application with some (or preferably all) of the information with respect to the relevant diagnostic test being performed.

Preferably at substantially the same time, in the sensing step (see method step 912 in FIG. 9), the test device 200 may preferably process quality control data and/or measurements. Test data is detected from the sample 50 using the sensor 214 of the test device 200.

In the data transmission step (see method step 912 in FIG. 9), the test data is electronically transmitted to the electronic connection element 410 of the electronic device 400 using the test connection element 216 of the test device 200. That is, the test device 200 transfers the test data to the electronic device 400.

In the processing step 914, the electronic device 400 preferably receives and analyzes test data for subsequent presentation of the data inside the aforesaid window and/or application. That is, in the processing step 914, one or more of the algorithms 202, 204 are applied to the test data using the processor 416 of the electronic device 400 to generate the highly sensitive and accurate quantitative test results and/or presentation data based on the quantitative test results. The presentation data so generated preferably includes the treatment and follow-up suggestion data based on the test results. As aforesaid, the treatment and follow-up suggestion data is preferably determined with reference to one or more of the algorithms 202, 204 stored onboard the electronic device 400 or the test device 200, or in one of the remote databases 800. Preferably, one or more of the algorithms 202, 204 generate the quantitative test results and/or the presentation data for presentation from the display element in the form of one or more visually presentable textual data, graphical data 702, or colored indicator light data. In the processing step 914, the test results may also be quantified as high, medium, and/or low results.

The ID storage step occurs before the identification step. In the ID storage step, the electronic device is used to store user identification data associated with the user 90 and/or an owner of the electronic device 400.

Preferably in the identification step 916, the patient or user 90 may preferably record his or her ID information through the biometrics identification element or directly through a keypad 412 of the electronic device 400, or through a camera or a microphone which may be provided in association with the electronic device 400. To put it another way, in the identification step 916, the identification element 300 is used to identify the user 90. Preferably, the user is biometrically identified. In the identification step 916, the identification element 300 also preferably automatically accesses the user identification data stored in the electronic device 400. Thereafter, in the ID analysis and recording step 918, patient identification analysis and recording is performed.

In the compilation and report design step 920, data compilation and report design is performed, preferably using the presentation data. Preferably thereafter, in the presentation step 922, the patient or user 90 (or other person) may preferably be provided with access to the test analysis, preferably via the screen of the electronic device 400. That is, the quantitative test results and/or the presentation data (e.g., the treatment and follow-up suggestion data) are presented to the user 90 using the presentation element 414 of the electronic device 400. Preferably, in the presentation step 922, the quantitative test results and/or the presentation data are presented from the display element of the presentation element 414.

Preferably after that, in the network transmission step 924, the system 100 may preferably provide an option (e.g. via presentation of a send command prompt 704 on the display element) to transfer onboard data to a remote database 800, to keep the data inside the electronic device 400, and/or to keep the data inside the test device 200. The network transmission step 924 occurs after the data transmission step. In the network transmission step 924, the electronic device 400 is used to automatically transmit the test data, the quantitative test results and/or the presentation data for recordal in one or more remote laboratory and/or hospital information systems 608.

The billing step occurs after the identification step 916. In the billing step, the account (associated with the user identification data stored in the electronic device 400) is debited in association with the generation of the quantitative test results.

Thereafter, in the use completion step 926, use of the test device 200 and the electronic device 400 ceases. In the disposal step, the test device 200 is disposed in a suitable waste facility 230. Alternately, the reagents 60 and/or biological components may be neutralized in a suitable recycling facility 240. Preferably in this step, the system 100 may query the user 90 to release the waste reagent and/or a waste reagent chamber 218 of the test device 200, or the system 100 may automatically release the waste reagents inside the test device 200. The sensor 214 and the test connection element 216 may be sterilized and re-used in the recycling facility 240.

This concludes the description of presently preferred embodiments of the invention. The foregoing description has been presented for the purpose of illustration and is not intended to be exhaustive or to limit the invention to the precise form disclosed. Other modifications, variations and alterations are possible in light of the above teaching and will be apparent to those skilled in the art, and may be used in the design and manufacture of other embodiments according to the present invention without departing from the spirit and scope of the invention. It is intended the scope of the invention be limited not by this description but only by the claims forming a part of this application and/or any patent issuing herefrom.

The invention claimed is:

1. An electronic device and single-use handheld diagnostic test device system, for use with a biological and/or environmental test sample, the system comprising:
    (a) a single-use handheld diagnostic test device adapted to receive and operatively react the sample with one or more reagents, with the test device having:
        (i) at least one sensor operatively detecting test data from the sample after reaction with the reagents; and
        (ii) a test connection element; and
    (b) an electronic device having:
        (i) a mating electronic connection element operatively connected with the test connection element and electronically receiving the test data from the test device;
        (ii) a processor operatively applying data analysis and quality control algorithms to control the reaction of the sample with the reagents, and operatively applying the data analysis and quality control algorithms to the test data to generate quantitative test results and presentation data based on the quantitative test results; and
        (iii) a presentation element operatively presenting to a user the presentation data based on the quantitative test results;
    (c) a connectivity interface adapted to operatively connect the test connection element and the electronic connection element;
    wherein the test device is adapted to test a single one said sample and is adapted for disposal, or for sterilization and re-use of the sensor and/or the test connection element, after the electronic device receives the test data; and wherein the test device has onboard memory which electronically stores the quality control algorithm and the test data; and wherein the processor of the electronic device operatively receives the test data and the quality control algorithm from the test device via the connectivity interface.

2. A system according to claim 1, further comprising an identification element operative to identify the user, with the identification element provided in the form of a standalone identification component and/or integrally with the electronic device and/or the test device.

3. A system according to claim 2, wherein the identification element comprises a biometric identification element, preferably a fingerprint scanner, a retinal scanner, a microphone and voice recognition element, a camera and facial recognition element, and/or a genetic expression factor identification element.

4. A system according to claim 1, wherein the electronic device stores user identification data associated with the user and/or an owner of the electronic device, and Wherein the identification element automatically accesses the user identification data stored in the electronic device.

5. An electronic device and single-use handheld diagnostic test device system, for use with a biological and/or environmental test sample, the system comprising:
 (a) a single-use handheld diagnostic test device adapted to receive and operatively react the sample with one or more reagents, with the test device having:
  (i) at least one sensor operatively detecting test data from the sample after reaction with the reagents; and
  (ii) a test connection element; and
 (b) an electronic device having:
  (i) a mating electronic connection element operatively connected with the test connection element and electronically receiving the test data from the test device;
  (ii) a processor operatively applying data analysis and quality control algorithms to control the reaction of the sample with the reagents, and operatively applying the data analysis and quality control algorithms to the test data to generate quantitative test results and presentation data based on the quantitative test results; and
  (iii) a presentation element operatively presenting to a user the presentation data based on the quantitative test results;
 (c) a connectivity interface adapted to operatively connect the test connection element and the electronic connection element;
 wherein the test device is adapted to test a single one said sample and is adapted for disposal, or for sterilization and re-use of the sensor and/or the test connection element, after the electronic device receives the test data and the quality control algorithm from the test device;
 further comprising an identification element operative to identify the user, with the identification element provided in the form of a standalone identification component and/or integrally with the electronic device and/or the test device;
 wherein the electronic device stores user identification data associated with the user and/or an owner of the electronic device, and wherein the identification element automatically accesses the user identification data stored in the electronic device; and
 adapted for use with an account associated with the user identification data, and further comprising a billing element operatively debiting the account in association with the generation of the quantitative test results.

6. A system according to claim 5, wherein the presentation element comprises a display element, and the algorithms generate the quantitative test results and/or the presentation data for presentation from the display element in the form of one or more visually presentable (a) textual data, (b) graphical data, and/or (c) colored indicator light data.

7. A system according to claim 5,
wherein the test results are quantified as high, medium, and/or low results.

8. A system according to claim 5,
wherein the test results are quantified as a positive or negative result.

9. A system according to claim 5,
wherein the test results are quantified to provide a diagnosis selected from a test result database comprising a plurality of diagnoses, each associated with a quantified range and wherein the quantified test results for the selected diagnosis is within the quantified range.

10. A system according to claim 5,
wherein the electronic device has a battery, and wherein the test connection element of the test device receives power, via the electronic connection element, from the battery.

11. A system according to claim 5, wherein the electronic device comprises: (a) a test reader device; (b) a cellular telephone; (c) a mobile communications device; (d) a personal digital assistant; (e) a desktop computer; (f) a laptop computer; (g) a navigation device; (h) a digital audio player; (i) a camera; (j) a gaming device; (k) a television; and/or (l) a radio.

12. A system according to claim 5, wherein the electronic device comprises a networking electronic device and automatically transmits the test data, the quantitative test results and/or the presentation data for recordal in one or more remote laboratory and/or hospital information systems.

13. A system according to claim 5,
wherein the presentation data presented to the user comprises treatment and follow-up suggestion data based on the test results.

14. A single-use handheld diagnostic test device system, for use with an electronic device having an electronic connection element, a presentation element, and a processor for operative application of data analysis and quality control algorithms, with the test device adapted to receive and operatively react a biological and/or environmental test sample with one or more reagents, wherein the test device comprises:
 (a) at least one sensor operatively detecting test data from the sample after reaction with the reagents;
 (b) a connectivity interface operatively connecting the test device and the electronic device; and
 (c) a mating test connection element operatively connected with, and electronically transmitting the quality control algorithm and the test data to the electronic device via, the connectivity interface operatively connected to the electronic connection element; such as to enable the processor to operatively apply the data analysis and quality control algorithms to control the reaction of the sample with the reagents, and operatively apply the data analysis and quality control algorithms to the test data for generation of quantitative test results and presentation data based on the quantitative test results, and such as to enable the presentation element to operatively present to a user the presentation data based on the quantitative test results; and wherein the test device is adapted to test a single one said sample and is adapted for disposal, or for sterilization and re-use of the sensor and/or the test connection element, after the electronic transmission of the test data to the electronic device via the connectivity interface; and further comprising onboard memory which electronically stores at least one of the quality control algorithm and the test data; and wherein the test connection element electronically transmits the quality control algorithm to the electronic connection element of the electronic device via the connectivity interface.

15. A device according to claim 14, further comprising an identification element operative to identify the user, with the identification element provided in the form of a standalone identification component and/or integrally with the sensor and/or the test connection element.

16. A device according to claim 15, wherein the identification element comprises a biometric identification element, preferably a fingerprint scanner, a retinal scanner, a microphone and voice recognition element, a camera and facial recognition element, and/or a genetic expression factor identification element.

17. A device according to claim 15, adapted for use with user identification data which is stored in the electronic device and is associated with the user and/or an owner of the electronic device, wherein the identification element automatically accesses the user identification data stored in the electronic device.

18. A single-use handheld diagnostic test device for use with an electronic device having an electronic connection element, a presentation element, and a processor for operative application of the data analysis and quality control algorithms, with the test device adapted to receive and operatively react a biological and/or environmental test sample with one or more reagents, wherein the test device comprises:
  (a) at least one sensor operatively detecting test data from the sample after reaction with the reagents;
  (b) a connectivity interface operatively connecting the test device and the electronic device; and
  (c) a mating test connection element operatively connected with, and electronically transmitting at least one of the quality control algorithm and the test data to the electronic device via, the connectivity interface operatively connected to the electronic connection element; such as to enable the processor to operatively apply the data analysis and quality control algorithms to control the reaction of the sample with the reagents, and operatively apply the data analysis and quality control algorithms to the test data for generation of quantitative test results and presentation data based on the quantitative test results, and such as to enable the presentation element to operatively present to a user the presentation data based on the quantitative test results;
wherein the test device is adapted to test a single one said sample and is adapted for disposal, or for sterilization and re-use of the sensor and/or the test connection element, after electronic transmission of the test data and the quality control algorithm from the test device to the electronic device via the connectivity interface;
further comprising an identification element operative to identify the user, with the identification element provided in the form of a standalone identification component and/or integrally with the sensor and/or the test connection element; adapted for use with user identification data which is stored in the electronic device and is associated with the user and/or an owner of the electronic device, wherein the identification element automatically accesses the user identification data stored in the electronic device; and adapted for use with an account associated with the user identification data, and further comprising a billing element operatively debiting the account in association with the generation of the quantitative test results.

19. A device according to claim 18, adapted for use with a display element as the presentation element, and wherein the algorithms are adapted to generate the quantitative test results and/or the presentation data for presentation from the display element in the form of one or more visually presentable (a) textual data, (b) graphical data, and/or (c) colored indicator light data.

20. A device according to claim 18, wherein the algorithms are adapted to quantify the test results as high, medium, and/or low results.

21. A device according to claim 18, wherein the algorithms are adapted to quantify the test results as a positive or negative result.

22. A device according to claim 18, wherein the algorithms are adapted to quantify the test results to provide a diagnosis selected from a test result database comprising a plurality of diagnoses, each associated with a quantified range and wherein the quantified test results for the selected diagnosis is within the quantified range.

23. A device according to claim 18, the device being adapted for use with a battery onboard the electronic device, wherein the test connection element of the test device receives power, via the connectivity interface operatively connected to the electronic connection element, from the battery.

24. A device according to claim 18, adapted for use with one or more of following as the electronic device: (a) a test reader device; (b) a cellular telephone; (c) a mobile communications device; (d) a personal digital assistant; (e) a desktop computer; (f) a laptop computer; (g) a navigation device; (h) a digital audio player; (i) a camera; (j) a gaming device; (k) a television; and/or (l) a radio.

25. A device according to claim 18, adapted for use with a networking electronic device as the electronic device, such as to enable the networking electronic device to automatically transmit the test data, the quantitative test results and/or the presentation data for recordal in one or more remote laboratory and/or hospital information systems.

26. A device according to claim 18, adapted for use with presentation data presented to the user which comprises treatment and follow-up suggestion data based on the test results.

27. An electronic device and single-use handheld diagnostic test device system, for use with a biological and/or environmental test sample, the system comprising:
  (a) a single-use handheld diagnostic test device adapted to receive and operatively react the sample with one or more reagents, with the test device having:
    (i) at least one sensor operatively detecting test data from the sample after reaction with the reagents; and
    (ii) a test connection element; and
  (b) an electronic device having:

(i) a mating electronic connection element operatively connected with the test connection element and electronically receiving the test data from the test device;
(ii) a processor operatively applying data analysis and quality control algorithms to control the reaction of the sample with the reagents, and operatively applying the data analysis and quality control algorithms to the test data to generate quantitative test results and presentation data based on the quantitative test results; and
(iii) a presentation element operatively presenting to a user the presentation data based on the quantitative test results;
wherein the test device is adapted to test a single one said sample and is adapted for disposal, or for sterilization and re-use of the sensor and/or the test connection element, after the electronic device receives the test data and the quality control algorithm from the test device;
further comprising an identification element operative to identify the user, with the identification element provided in the form of a standalone identification component and/or integrally with the electronic device and/or the test device;
wherein the electronic device stores user identification data associated with the user and/or an owner of the electronic device, and wherein the identification element automatically accesses the user identification data stored in the electronic device;
adapted for use with an account associated with the user identification data, and further comprising a billing element operatively debiting the account in association with the generation of the quantitative test results; and
wherein the test results are quantified as a positive or negative result.

28. An electronic device and single-use handheld diagnostic test device system, for use with a biological and/or environmental test sample, the system comprising:
(a) a single-use handheld diagnostic test device adapted to receive and operatively react the sample with one or more reagents, with the test device having:
(i) at least one sensor operatively detecting test data from the sample after reaction with the reagents; and
(ii) a test connection element; and
(b) an electronic device having:
(i) a mating electronic connection element operatively connected with the test connection element and electronically receiving the test data from the test device;
(ii) a processor operatively applying data analysis and quality control algorithms to control the reaction of the sample with the reagents, and operatively applying the data analysis and quality control algorithms to the test data to generate quantitative test results and presentation data based on the quantitative test results; and
(iii) a presentation element operatively presenting to a user the presentation data based on the quantitative test results;
wherein the test device is adapted to test a single one said sample and is adapted for disposal, or for sterilization and re-use of the sensor and/or the test connection element, after the electronic device receives the test data and the quality control algorithm from the test device;
further comprising an identification element operative to identify the user, with the identification element provided in the form of a standalone identification component and/or integrally with the electronic device and/or the test device;
wherein the electronic device stores user identification data associated with the user and/or an owner of the electronic device, and wherein the identification element automatically accesses the user identification data stored in the electronic device;
adapted for use with an account associated with the user identification data, and further comprising a billing element operatively debiting the account in association with the generation of the quantitative test results; and
wherein the test results are quantified to provide a diagnosis selected from a test result database comprising a plurality of diagnoses, each associated with a quantified range and wherein the quantified test results for the selected diagnosis is within the quantified range.

29. A single-use handheld diagnostic test device for use with an electronic device having an electronic connection element, a presentation element, and a processor for operative application of the data analysis and quality control algorithms, with the test device adapted to receive and operatively react a biological and/or environmental test sample with one or more reagents, wherein the test device comprises:
(a) at least one sensor operatively detecting test data from the sample after reaction with the reagents; and
(b) a mating test connection element operatively connected with, and electronically transmitting at least one of the quality control algorithm and the test data to the electronic device via, the electronic connection element; such as to enable the processor to operatively apply the data analysis and quality control algorithms to control the reaction of the sample with the reagents, and operatively apply the data analysis and quality control algorithms to the test data for generation of quantitative test results and presentation data based on the quantitative test results, and such as to enable the presentation element to operatively present to a user the presentation data based on the quantitative test results;
wherein the test device is adapted to test a single one said sample and is adapted for disposal, or for sterilization and re-use of the sensor and/or the test connection element, after electronic transmission of the test data and the quality control algorithm from the test device to the electronic device;
further comprising an identification element operative to identify the user, with the identification element provided in the form of a standalone identification component and/or integrally with the sensor and/or the test connection element;
adapted for use with user identification data which is stored in the electronic device and is associated with the user and/or an owner of the electronic device, wherein the identification element automatically accesses the user identification data stored in the electronic device; and
adapted for use with an account associated with the user identification data, and further comprising a billing element operatively debiting the account in association with the generation of the quantitative test results; and
wherein the algorithms are adapted to quantify the test results as a positive or negative result.

30. A single-use handheld diagnostic test device for use with an electronic device having an electronic connection element, a presentation element, and a processor for operative application of the data analysis and quality control algorithms, with the test device adapted to receive and operatively react a biological and/or environmental test sample with one or more reagents, wherein the test device comprises:
- (a) at least one sensor operatively detecting test data from the sample after reaction with the reagents; and
- (b) a mating test connection element operatively connected with, and electronically transmitting at least one of the quality control algorithm and the test data to the electronic device via, the electronic connection element; such as to enable the processor to operatively apply the data analysis and quality control algorithms to control the reaction of the sample with the reagents, and operatively apply the data analysis and quality control algorithms to the test data for generation of quantitative test results and presentation data based on the quantitative test results, and such as to enable the presentation element to operatively present to a user the presentation data based on the quantitative test results;

wherein the test device is adapted to test a single one said sample and is adapted for disposal, or for sterilization and re-use of the sensor and/or the test connection element, after electronic transmission of the test data and the quality control algorithm from the test device to the electronic device;

further comprising an identification element operative to identify the user, with the identification element provided in the form of a standalone identification component and/or integrally with the sensor and/or the test connection element;

adapted for use with user identification data which is stored in the electronic device and is associated with the user and/or an owner of the electronic device, wherein the identification element automatically accesses the user identification data stored in the electronic device; and adapted for use with an account associated with the user identification data, and further comprising a billing element operatively debiting the account in association with the generation of the quantitative test results; and wherein the algorithms are adapted to quantify the test results to provide a diagnosis selected from a test result database comprising a plurality of diagnoses, each associated with a quantified range and wherein the quantified test results for the selected diagnosis is within the quantified range.

\* \* \* \* \*